(12) United States Patent
Needham et al.

(10) Patent No.: US 10,955,414 B2
(45) Date of Patent: Mar. 23, 2021

(54) IMMUNOASSAY METHODS AND COMPOSITIONS FOR DETECTING INFECTION INVOLVING USE OF TEST ANTIGENS AS CROSS-REACTIVE CONTROL ANTIGENS

(71) Applicant: InBios International, Inc., Seattle, WA (US)

(72) Inventors: James William Needham, Seattle, WA (US); Syamal Raychaudhuri, Seattle, WA (US)

(73) Assignee: InBios International, Inc., Seattle, WA (US)

( * ) Notice: Subject to any disclaimer, the term of this patent is extended or adjusted under 35 U.S.C. 154(b) by 0 days.

(21) Appl. No.: 16/321,284

(22) PCT Filed: Aug. 1, 2017

(86) PCT No.: PCT/US2017/044950
§ 371 (c)(1),
(2) Date: Jan. 28, 2019

(87) PCT Pub. No.: WO2018/026845
PCT Pub. Date: Feb. 8, 2018

(65) Prior Publication Data
US 2019/0170751 A1 Jun. 6, 2019

Related U.S. Application Data

(60) Provisional application No. 62/369,723, filed on Aug. 1, 2016.

(51) Int. Cl.
*C12Q 1/70* (2006.01)
*G01N 33/569* (2006.01)
(Continued)

(52) U.S. Cl.
CPC ... *G01N 33/56983* (2013.01); *C07K 16/1081* (2013.01); *C07K 16/4283* (2013.01);
(Continued)

(58) Field of Classification Search
None
See application file for complete search history.

(56) References Cited

U.S. PATENT DOCUMENTS

2011/0189155 A1 8/2011 Brehin et al.
2015/0086978 A1 3/2015 Raychaudhuri et al.

FOREIGN PATENT DOCUMENTS

WO WO 2016/070178 A1 5/2016
WO WO 2018/026845 A1 2/2018

OTHER PUBLICATIONS

Frank, "Chapter 4: Specificity and Cross-Reactivity," Immunology and Evolution of Infectious Diseases. Princeton (NJ): Princeton University Press, available at: https://www.ncbi.nlm.nih.gov/books/NBK2396/ (Year: 2002).*

(Continued)

*Primary Examiner* — M Franco G Salvoza
(74) *Attorney, Agent, or Firm* — Seed IP Law Group LLP

(57) ABSTRACT

The present invention relates to compositions and methods involving diagnostic tests with multiple test antigens. The present invention involves the expanded use of test antigens as cross-reactive control antigens (CCAs). The invention advantageously provides for enhanced test results analysis by simultaneously providing both test antigen and CCA signal results. These results, in turn, allow useful sample comparison and cross-reference between samples to more accurately identify and verify the fidelity of test results obtained for multiple infective agents at once. The present invention may include compositions and methods for detecting infection by Zika virus or another flavivirus, and may (Continued)

distinguish between infections caused by genetically similar agents.

21 Claims, 14 Drawing Sheets

(51) Int. Cl.
    C07K 16/10    (2006.01)
    C07K 16/42    (2006.01)
    G01N 33/543   (2006.01)
    G01N 33/558   (2006.01)
    G01N 33/563   (2006.01)
(52) U.S. Cl.
    CPC ......... G01N 33/543 (2013.01); G01N 33/558
        (2013.01); G01N 33/563 (2013.01); G01N
        2333/183 (2013.01); G01N 2469/20 (2013.01);
        Y02A 50/30 (2018.01)

(56) References Cited

OTHER PUBLICATIONS

Rudikoff et al., "Single amino acid substitution altering antigen-binding specificity," Proc Natl Acad Sci USA 79:1979-1983 (Year: 1982).*
Chao et al., "Nonstructural Protein 1—Specific Immunoglobulin M and G Antibody Capture Enzyme-Linked Immunosorbent Assays in Diagnosis of Flaviviral Infections in Humans," Journal of Clinical Microbiology 53(2): 557-566, 2015.
Galula et al., "Establishment of an Algorithm Using prM/E- and NS1-Specific IgM Antibody-Capture Enzyme-Linked Immunosorbent Assays in Diagnosis of Japanese Encephalitis Virus and West Nile Virus Infections in Humans," Journal of Clinical Microbiology 54(2): 412-422, 2016.
Li et al., "[[Virus-like particle-based immunoglobulin M capture enzyme-linked immunosorbent assay for the detection of IgM antibodies against Chikungunya virus]," Bing Du Xue Bao 30(6): 599-604, 2014, Abstract Only (1 page).
Allison et al., "Synthesis and Secretion of Recombinant Tick-Borne Encephalitis Virus Protein E in Soluble and Particulate Form," Journal of Virology 69(9): 5816-5820, 1995.
Allison et al., "Two Distinct Size Classes of Immature and Mature Subviral Particles from Tick-Borne Encephalitis Virus," Journal of Virology 77(21): 11357-11366, 2003.
Chang et al., "A Single Intramuscular Injection of Recombinant Plasmid DNA Induces Protective Immunity and Prevents Japanese Encephalitis in Mice," Journal of Virology 74(9): 4244-4252, 2000.

Chang et al., "Enhancing biosynthesis and secretion of premembrane and envelope proteins by the chimeric plasmid of dengue virus type 2 and Japanese encephalitis virus," Virology 306: 170-180, 2003.
Corpet, "Multiple sequence alignment with hierarchical clustering," Nucleic Acids Research 16(22): 10881-10890, 1988.
Davis et al., "West Nile Virus Recombinant DNA Vaccine Protects Mouse and Horse from Virus Challenge and Expresses In Vitro a Noninfectious Recombinant Antigen That Can Be Used in Enzyme-Linked Immunosorbent Assays," Journal of Virology 75(9): 4040-4047, 2001.
Higgins et al., "CLUSTAL: a package for performing multiple sequence alignment on a microcomputer," Gene 73: 237-244, 1988.
Higgins et al., "Fast and sensitive multiple sequence alignments on a microcomputer," CABIOS Communications 5(2): 151-153, 1989.
Huang et al., "Parallelization of a local similarity algorithm," CABIOS 8(2): 155-165, 1992.
Hunt et al., "A recombinant particulate antigen of Japanese encephalitis virus produced in stably-transformed cells is an effective noninfectious antigen and subunit immunogen," Journal of Virological Methods* 97: 133-149, 2001.
Konishi et al., "Induction of Protective Immunity against Japanese Encephalitis in Mice by Immunization with a Plasmid Encoding Japanese Encephalitis Virus Premembrane and Envelope Genes," *Journal of Virology* 72(6): 4925-4930, 1998.
Konishi et al., "Evidence for antigen production in muscles by dengue and Japanese encephalitis DNA vaccines and a relation to their immunogenicity in mice," *Vaccine* 21: 3713-3720, 2003.
Kuno et al., "Full-length sequencing and genomic characterization of Bagaza, Kedougou, and Zika viruses," *Arch. Virol.* 152: 687-696, 2007.
Needleman et al., "A General Method Applicable to the Search for Similarities in the Amino Acid Sequence of Two Proteins," *J. Mol. Biol.* 48: 443-453, 1970.
Pearson et al., "Improved tools for biological sequence comparison," *Proc. Natl. Acad. Sci. USA* 85: 2444-2448, 1988.
Pearson, *Methods in Molecular Biology, vol. 24: Computer Analysis of Sequence Data, Part 1*, Humana Press Inc., Totowa, New Jersey, 1994, Chapter 26, "Using the FASTA Program to Search Protein and DNA Sequence Databases," 307-331.
Purdy et al., "Secretion of noninfectious dengue virus-like particles and identification of amino acids in the stem region involved in intracellular retention of envelope protein," *Virology* 333: 239-250, 2005.
Schalich et al., "Recombinant Subviral Particles from Tick-Borne Encephalitis Virus Are Fusogenic and Provide a Model System for Studying Flavivirus Envelope Glycoprotein Functions," *Journal of Virology* 70(7): 4549-4557, 1996.
Smith et al., "Comparison of Biosequences," *Advances in Applied Mathematics* 2: 482-489, 1981.

* cited by examiner

Example Plate Layout

An example plate layout is shown below which indicates a method for screening 28 specimens against Zika Ag, CCA and NCA.

| | 1 | 2 | 3 | 4 | 5 | 6 | 7 | 8 | 9 | 10 | 11 | 12 |
|---|---|---|---|---|---|---|---|---|---|---|---|---|
| A | Positive Control | Sample #5 | Sample #13 | Sample #21 | Positive Control | Sample #5 | Sample #13 | Sample #21 | Positive Control | Sample #5 | Sample #13 | Sample #21 |
| B | Positive Control | Sample #6 | Sample #14 | Sample #22 | Positive Control | Sample #6 | Sample #14 | Sample #22 | Positive Control | Sample #6 | Sample #14 | Sample #22 |
| C | Negative Control | Sample #7 | Sample #15 | Sample #23 | Negative Control | Sample #7 | Sample #15 | Sample #23 | Negative Control | Sample #7 | Sample #15 | Sample #23 |
| D | Negative Control | Sample #8 | Sample #16 | Sample #24 | Negative Control | Sample #8 | Sample #16 | Sample #24 | Negative Control | Sample #8 | Sample #16 | Sample #24 |
| E | Sample #1 | Sample #9 | Sample #17 | Sample #25 | Sample #1 | Sample #9 | Sample #17 | Sample #25 | Sample #1 | Sample #9 | Sample #17 | Sample #25 |
| F | Sample #2 | Sample #10 | Sample #18 | Sample #26 | Sample #2 | Sample #10 | Sample #18 | Sample #26 | Sample #2 | Sample #10 | Sample #18 | Sample #26 |
| G | Sample #3 | Sample #11 | Sample #19 | Sample #27 | Sample #3 | Sample #11 | Sample #19 | Sample #27 | Sample #3 | Sample #11 | Sample #19 | Sample #27 |
| H | Sample #4 | Sample #12 | Sample #20 | Sample #28 | Sample #4 | Sample #12 | Sample #20 | Sample #28 | Sample #4 | Sample #12 | Sample #20 | Sample #28 |

Ready to Use ZIKV Antigen (Zika Ag) — columns 1–4
Cross-reactive Control Antigen (CCA) — columns 5–8
Normal Cell Antigen (NCA) — columns 9–12

*Fig. 2*

Zika Interpretation Table

| ISR Analysis | | NCA Analysis | | Result Interpretation and Follow-up Testing | |
|---|---|---|---|---|---|
| Initial Result | Zika ISR After Re-Test | Zika/NCA | CCA/NCA | Final Interpretation* | Follow-up Testing |
| Zika ISR ≥1.80 — Reactive for Zika IgM | No Re-Test Required | No NCA Analysis Required | No NCA Analysis Required | Presumptive Zika Positive — Presence of detectable Zika IgM antibody, possible recent infection with ZIKV | The result should be confirmed by the latest CDC testing algorithms**. |
| | Mean ≥1.70 Reactive for Zika IgM (No NCA Analysis Required) | ≥1.70 | ≥1.70 | Possible Zika Positive† Zika virus IgM: Detected Flavivirus IgM: Detected | The result should be confirmed by the latest CDC testing algorithms**. |
| | | | <1.70 | Possible Zika Positive† Zika virus IgM: Detected Flavivirus IgM: Not Detected | The result should be confirmed by the latest CDC testing algorithms**. |

*Fig. 3A*

Zika Interpretation Table

| Zika ISR | ISR Analysis | | NCA Analysis | | Result Interpretation and Follow-up Testing | |
|---|---|---|---|---|---|---|
| | Initial Result | Zika ISR After Re-Test | Zika/NCA | CCA/NCA | Final Interpretation* | Follow-up Testing |
| 1.80 - 1.60 | Re-Test (in Duplicate) | Mean <1.70 (NCA Analysis Required) | <1.70 | ≥1.70 | Presumptive Other Flavivirus Positive Zika virus IgM: Not Detected Flavivirus IgM: Detected | The result should be confirmed with FDA-cleared Dengue and West Nile virus IgM devices. |
| ≤1.60 | NCA Analysis Required | No Re-Test Required | | <1.70 | Negative Zika virus IgM: Not Detected Flavivirus IgM: Not Detected | None# |

†Specimens that fall in this category may still have levels of Zika IgM antibody present in serum and follow-up testing is required; however, other confounding IgM antibodies from related flaviviruses may be present that cause this level of reactivity.

*All Zika virus IgM detected and Flavivirus IgM detected results are presumptive positive results.

** For information regarding Zika testing algorithms, please refer to CDC guidance for state and local public health laboratories: https://www.cdc.gov/zika/laboratories/index.html

Negative results with specimens collected before 8 days after onset of symptoms should be repeated with a later bleed taken at least 7 days from the first specimen. In addition, in the case of pregnant women please follow the latest CDC interim pregnancy guidance for healthcare providers regarding clinical management of negative results (https://www.cdc.gov/zika/hc-providers/index.html).

*Fig. 3B*

| | Sample ID | Raw OD$_{450}$ | | | | | | Zika Analysis (Evaluating Zika Antigen, CCA and NCA as an example ONLY) | | |
|---|---|---|---|---|---|---|---|---|---|---|
| | | Zika Antigen | Cross-reactive Control Antigen | Normal Control Antigen | West Nile Antigen | Dengue Antigen | Chik Antigen | Zika ISR (Zika / CCA) | CCA / NCA | Zika Interpretation ? |
| Controls | Positive Control | 2.989 | 0.202 | 0.055 | 0.142 | 0.229 | 0.282 | 14.77 | 3.67 | Zika Positive |
| | Negative Control | 0.067 | 0.065 | 0.056 | 0.062 | 0.060 | 0.220 | 1.03 | 1.15 | Negative |
| Zika Positive Sera | Zika - #1 | 1.065 | 0.073 | 0.056 | 0.064 | 0.074 | 0.176 | 14.61 | 1.31 | Zika Positive |
| | Zika - #2 | 1.063 | 0.069 | 0.055 | 0.063 | 0.069 | 0.102 | 15.48 | 1.25 | Zika Positive |
| | Zika - #3 | 0.580 | 0.082 | 0.060 | 0.066 | 0.081 | 0.369 | 7.11 | 1.36 | Zika Positive |
| | Zika - #4 | 1.588 | 0.134 | 0.057 | 0.062 | 0.150 | 0.157 | 11.87 | 2.37 | Zika Positive |
| | Zika - #5 | 0.639 | 0.076 | 0.058 | 0.059 | 0.081 | 0.113 | 8.36 | 1.33 | Zika Positive |
| | Zika - #6 | 0.287 | 0.112 | 0.059 | 0.070 | 0.127 | 0.302 | 2.56 | 1.90 | Zika Positive |
| | Zika - #7 | 0.569 | 0.065 | 0.057 | 0.062 | 0.062 | 0.173 | 8.72 | 1.14 | Zika Positive |
| | Zika - #8 | 0.967 | 0.085 | 0.059 | 0.070 | 0.083 | 0.174 | 11.43 | 1.42 | Zika Positive |
| | Zika - #9 | 0.255 | 0.083 | 0.056 | 0.070 | 0.091 | 0.189 | 3.05 | 1.50 | Zika Positive |
| | Zika - #10 | 0.262 | 0.064 | 0.055 | 0.061 | 0.067 | 0.142 | 4.12 | 1.16 | Zika Positive |

Fig. 4A

|  | Sample ID | Zika Antigen | Cross-reactive Control Antigen | Normal Control Antigen | West Nile Antigen | Dengue Antigen | Chik Antigen | Zika ISR (Zika/CCA) | CCA/NCA | Zika Interpretation |
|---|---|---|---|---|---|---|---|---|---|---|
|  |  | Raw OD450 | | | | | | Zika Analysis (Evaluating Zika Antigen, CCA and NCA as an example ONLY) | | |
| West Nile Positive Sera | WN #1 | 0.482 | 2.542 | 0.057 | 2.741 | 0.500 | 0.082 | 0.19 | 44.44 | Other Flavivirus |
|  | WN #2 | 0.642 | 2.200 | 0.056 | 2.243 | 0.371 | 0.069 | 0.29 | 39.63 | Other Flavivirus |
|  | WN #3 | 0.262 | 2.183 | 0.057 | 2.407 | 0.378 | 0.125 | 0.12 | 38.57 | Other Flavivirus |
|  | WN #4 | 0.320 | 1.495 | 0.058 | 1.517 | 0.312 | 0.186 | 0.21 | 25.69 | Other Flavivirus |
|  | WN #5 | 0.787 | 1.557 | 0.054 | 1.629 | 0.460 | 0.127 | 0.51 | 28.83 | Other Flavivirus |
|  | WN #6 | 0.407 | 2.678 | 0.058 | 3.078 | 0.306 | 0.127 | 0.15 | 46.34 | Other Flavivirus |
|  | WN #7 | 0.293 | 1.478 | 0.062 | 1.638 | 0.212 | 0.112 | 0.20 | 23.92 | Other Flavivirus |
|  | WN #8 | 0.571 | 2.539 | 0.058 | 2.631 | 0.537 | 0.094 | 0.22 | 44.09 | Other Flavivirus |
|  | WN #9 | 0.595 | 2.898 | 0.056 | 3.107 | 0.467 | 0.125 | 0.21 | 51.75 | Other Flavivirus |
|  | WN #10 | 0.159 | 1.633 | 0.061 | 1.792 | 0.183 | 0.121 | 0.10 | 26.67 | Other Flavivirus |
| Dengue Positive Sera | Dengue #1 | 0.276 | 0.739 | 0.056 | 0.171 | 0.790 | 0.126 | 0.37 | 13.26 | Other Flavivirus |
|  | Dengue #2 | 0.803 | 1.195 | 0.062 | 0.327 | 1.378 | 0.130 | 0.67 | 19.27 | Other Flavivirus |
|  | Dengue #3 | 0.378 | 1.773 | 0.057 | 0.175 | 2.203 | 0.159 | 0.21 | 31.10 | Other Flavivirus |
|  | Dengue #4 | 0.373 | 1.059 | 0.055 | 0.143 | 1.317 | 0.124 | 0.35 | 19.12 | Other Flavivirus |
|  | Dengue #5 | 0.462 | 1.235 | 0.055 | 0.274 | 1.457 | 0.664 | 0.37 | 22.33 | Other Flavivirus |
|  | Dengue #6 | 0.492 | 2.460 | 0.055 | 0.174 | 3.056 | 0.191 | 0.20 | 44.64 | Other Flavivirus |
|  | Dengue #7 | 1.068 | 2.084 | 0.058 | 0.481 | 2.399 | 0.164 | 0.51 | 36.25 | Other Flavivirus |
|  | Dengue #8 | 0.512 | 1.646 | 0.057 | 0.217 | 2.053 | 0.117 | 0.31 | 28.73 | Other Flavivirus |
|  | Dengue #9 | 0.576 | 1.151 | 0.058 | 0.916 | 1.273 | 0.112 | 0.50 | 19.92 | Other Flavivirus |
|  | Dengue #10 | 0.685 | 1.720 | 0.070 | 0.400 | 2.043 | 0.112 | 0.40 | 24.75 | Other Flavivirus |

Fig. 4B

| | Sample ID | Raw OD$_{450}$ | | | | | | Zika Analysis (Evaluating Zika Antigen, CCA and NCA as an example ONLY) | |
|---|---|---|---|---|---|---|---|---|---|
| | | Zika Antigen | Cross-reactive Control Antigen | Normal Control Antigen | West Nile Antigen | Dengue Antigen | Chik Antigen | Zika ISR (Zika / CCA) | CCA / NCA | Zika Interpretation? |
| Chikungunya Positive Sera | Chik #1 | 0.080 | 0.083 | 0.105 | 0.073 | 0.084 | 4.000 | 0.96 | 0.79 | Negative |
| | Chik #2 | 0.080 | 0.192 | 0.057 | 0.069 | 0.239 | 4.000 | 0.42 | 3.39 | Other Flavivirus |
| | Chik #3 | 0.086 | 0.120 | 0.055 | 0.069 | 0.134 | 3.818 | 0.72 | 2.21 | Negative |
| | Chik #4 | 0.068 | 0.064 | 0.055 | 0.061 | 0.063 | 0.986 | 1.07 | 1.15 | Negative |
| | Chik #5 | 0.087 | 0.085 | 0.058 | 0.067 | 0.090 | 2.299 | 1.02 | 1.46 | Negative |
| | Chik #6 | 0.075 | 0.076 | 0.055 | 0.064 | 0.075 | 3.982 | 0.98 | 1.37 | Negative |
| | Chik #7 | 0.069 | 0.070 | 0.062 | 0.062 | 0.063 | 4.000 | 0.98 | 1.14 | Negative |
| | Chik #8 | 0.066 | 0.172 | 0.060 | 0.099 | 0.192 | 4.000 | 0.38 | 2.86 | Negative |
| | Chik #9 | 0.094 | 0.097 | 0.056 | 0.072 | 0.086 | 3.480 | 0.97 | 1.74 | Negative |
| | Chik #10 | 0.086 | 0.106 | 0.069 | 0.084 | 0.148 | 3.296 | 0.81 | 1.53 | Negative |
| Normal Human Serum | Normal serum #1 | 0.071 | 0.065 | 0.056 | 0.064 | 0.065 | 0.169 | 1.10 | 1.16 | Negative |
| | Normal serum #2 | 0.185 | 0.073 | 0.059 | 0.060 | 0.072 | 0.128 | 2.55 | 1.24 | Negative |
| | Normal serum #3 | 0.074 | 0.157 | 0.065 | 0.090 | 0.186 | 0.150 | 0.47 | 2.42 | Negative |
| | Normal serum #4 | 0.066 | 0.065 | 0.055 | 0.062 | 0.058 | 0.125 | 1.01 | 1.18 | Negative |
| | Normal serum #5 | 0.095 | 0.086 | 0.058 | 0.067 | 0.078 | 0.251 | 1.11 | 1.49 | Negative |
| | Normal serum #6 | 0.069 | 0.064 | 0.058 | 0.061 | 0.065 | 0.131 | 1.08 | 1.10 | Negative |

*Fig. 4C*

| | Sample ID | Threshold Used: 1.7 WN ISR (WN Antigen / Dengue Antigen) | Threshold used = 4.0 Dengue ISR (Dengue Antigen / WN Antigen) | Threshold Used = 5.0 Chik ISR (Chik Antigen / Dengue Antigen) | Interpretation (for WN, Dengue, Chik)? |
|---|---|---|---|---|---|
| Controls | Positive Control | 0.62 | 1.61 | 1.23 | Negative |
| | Negative Control | 1.04 | 0.96 | 3.68 | Negative |
| Zika Positive Sera | Zika - #1 | 0.87 | 1.16 | 2.39 | Negative |
| | Zika - #2 | 0.91 | 1.10 | 1.48 | Negative |
| | Zika - #3 | 0.82 | 1.22 | 4.55 | Negative |
| | Zika - #4 | 0.42 | 2.41 | 1.05 | Negative |
| | Zika - #5 | 0.72 | 1.39 | 1.40 | Negative |
| | Zika - #6 | 0.55 | 1.81 | 2.38 | Negative |
| | Zika - #7 | 0.99 | 1.01 | 2.78 | Negative |
| | Zika - #8 | 0.85 | 1.18 | 2.10 | Negative |
| | Zika - #9 | 0.77 | 1.30 | 2.07 | Negative |
| | Zika - #10 | 0.91 | 1.10 | 2.11 | Negative |

*Fig. 5A*

| | | Threshold Used: 1.7 | Threshold used = 4.0 | Threshold Used = 5.0 | |
|---|---|---|---|---|---|
| | Sample ID | WN ISR (WN Antigen / Dengue Antigen) | Dengue ISR (Dengue Antigen / WN Antigen) | Chik ISR (Chik Antigen / Dengue Antigen) | Interpretation (for WN, Dengue, Chik)? |
| West Nile Positive Sera | WN #1 | 3.48 | 0.18 | 0.16 | WN Positive |
| | WN #2 | 6.04 | 0.17 | 0.19 | WN Positive |
| | WN #3 | 6.36 | 0.16 | 0.33 | WN Positive |
| | WN #4 | 4.86 | 0.21 | 0.60 | WN Positive |
| | WN #5 | 3.54 | 0.28 | 0.28 | WN Positive |
| | WN #6 | 10.05 | 0.10 | 0.41 | WN Positive |
| | WN #7 | 7.71 | 0.13 | 0.53 | WN Positive |
| | WN #8 | 4.90 | 0.20 | 0.17 | WN Positive |
| | WN #9 | 6.65 | 0.15 | 0.27 | WN Positive |
| | WN #10 | 9.81 | 0.10 | 0.66 | WN Positive |

Fig. 5B

| Sample ID | Threshold Used: 1.7<br>WN ISR (WN Antigen / Dengue Antigen) | Threshold used = 4.0<br>Dengue ISR (Dengue Antigen / WN Antigen) | Threshold Used = 5.0<br>Chik ISR (Chik Antigen / Dengue Antigen) | Interpretation (for WN, Dengue, Chik)? |
|---|---|---|---|---|
| Dengue Positive Sera | | | | |
| Dengue #1 | 0.22 | 4.61 | 0.16 | Dengue Positive |
| Dengue #2 | 0.24 | 4.22 | 0.09 | Dengue Positive |
| Dengue #3 | 0.08 | 12.58 | 0.07 | Dengue Positive |
| Dengue #4 | 0.11 | 9.24 | 0.09 | Dengue Positive |
| Dengue #5 | 0.19 | 5.31 | 0.46 | Dengue Positive |
| Dengue #6 | 0.06 | 17.52 | 0.06 | Dengue Positive |
| Dengue #7 | 0.20 | 4.99 | 0.07 | Dengue Positive |
| Dengue #8 | 0.11 | 9.47 | 0.06 | Dengue Positive |
| Dengue #9 | 0.72 | 1.39 | 0.09 | Negative |
| Dengue #10 | 0.20 | 5.11 | 0.05 | Dengue Positive |

Fig. 5C

| Sample ID | Threshold Used: 1.7<br>WN ISR (WN Antigen / Dengue Antigen) | Threshold used = 4.0<br>Dengue ISR (Dengue Antigen / WN Antigen) | Threshold Used = 5.0<br>Chik ISR (Chik Antigen / Dengue Antigen) | Interpretation (for WN, Dengue, Chik)? |
|---|---|---|---|---|
| Chik #1 | 0.87 | 1.14 | 47.73 | Chikungunya Positive |
| Chik #2 | 0.29 | 3.45 | 16.77 | Chikungunya Positive |
| Chik #3 | 0.51 | 1.95 | 28.47 | Chikungunya Positive |
| Chik #4 | 0.97 | 1.03 | 15.78 | Chikungunya Positive |
| Chik #5 | 0.74 | 1.36 | 25.44 | Chikungunya Positive |
| Chik #6 | 0.85 | 1.17 | 53.16 | Chikungunya Positive |
| Chik #7 | 0.98 | 1.02 | 63.49 | Chikungunya Positive |
| Chik #8 | 0.52 | 1.94 | 20.88 | Chikungunya Positive |
| Chik #9 | 0.84 | 1.19 | 40.65 | Chikungunya Positive |
| Chik #10 | 0.56 | 1.77 | 22.27 | Chikungunya Positive |

Chikungunya Positive Sera

Fig. 5D

| Sample ID | | Threshold Used: 1.7<br>WN ISR (WN Antigen / Dengue Antigen) | Threshold used = 4.0<br>Dengue ISR (Dengue Antigen / WN Antigen) | Threshold Used = 5.0<br>Chik ISR (Chik Antigen / Dengue Antigen) | Interpretation (for WN, Dengue, Chik)? |
|---|---|---|---|---|---|
| Normal Human Serum | Normal serum #1 | 0.99 | 1.01 | 2.60 | Negative |
| | Normal serum #2 | 0.84 | 1.18 | 1.78 | Negative |
| | Normal serum #3 | 0.48 | 2.08 | 0.80 | Negative |
| | Normal serum #4 | 1.08 | 0.93 | 2.15 | Negative |
| | Normal serum #5 | 0.85 | 1.17 | 3.20 | Negative |
| | Normal serum #6 | 0.94 | 1.06 | 2.01 | Negative |

Fig. 5E

IMMUNOASSAY METHODS AND COMPOSITIONS FOR DETECTING INFECTION INVOLVING USE OF TEST ANTIGENS AS CROSS-REACTIVE CONTROL ANTIGENS

TECHNICAL FIELD

The present invention relates to compositions and methods involving diagnostic tests with multiple test antigens. Specifically, this invention relates to diagnostic compositions and methods involving the expanded use of test antigens as cross-reactive control antigens (CCAs). The diagnostic test compositions and methods described herein advantageously provide for enhanced test results analysis by simultaneously providing both test antigen and CCA signal results. These results, in turn, allow useful sample comparison and cross-reference between samples to more accurately identify test results obtained for multiple infective agents at once. The present invention in a particular embodiment relates generally to compositions and methods for detecting infection by an infectious agent, such as Flavivirus, including Zika virus, and also distinguishing infections caused by genetically similar agents or presenting in subjects with similar symptomology.

BACKGROUND

Zika virus disease (Zika) is a disease caused by Zika virus that is spread to people primarily through the bite of an infected mosquito from the *Aedes* genus, mainly *Aedes aegypti* in tropical regions. This is the same mosquito species that transmits dengue, chikungunya, and yellow fever. Common symptoms of Zika are fever, rash, joint pain, and conjunctivitis (red eyes). The illness is usually mild with symptoms lasting for several days to a week after being bitten by an infected mosquito.

The Zika virus was first discovered in 1947 and is named after the Zika forest in Uganda. In 1952, the first human cases of Zika were detected and since then, outbreaks of Zika have been reported in tropical Africa, Southeast Asia, and the Pacific Islands. Zika outbreaks have probably occurred in many locations but remain unrecognized because the symptoms are similar to many other diseases such as dengue and chikungunya. In May 2015, the Pan American Health Organization (PAHO) issued an alert regarding the first confirmed Zika virus infection in Brazil and on Feb. 1, 2016, the World Health Organization (WHO) declared Zika virus a public health emergency of international concern (PHEIC). Local transmission has been reported in many other countries and territories.

Of major concern is the effect the Zika virus may have on pregnant women. There is currently a very strong link between the Zika virus in pregnant women and the increase in the number of cases of babies born with microcephaly in Brazil and other countries, which is causing alarm worldwide. Sexual transmission of Zika virus is also of great concern, and in the United States cases of women contracting the disease from their partners have been reported.

In 2004, Chikungunya virus (CHIKV) reemerged from Africa and spread to the Indian Ocean Basin, Asia, and Europe causing explosive epidemics affecting millions of people. Chikungunya fever is characterized by severe, debilitating, and often chronic arthralgia that can persist for years, resulting in major economic as well as public health impacts. Additionally, CHIK fever is not easily diagnosed due to the overlap in initial signs and symptoms with dengue, malaria and other acute febrile illnesses, as well as the lack of high quality, affordable, commercially-available diagnostic assays.

The majority of people infected with CHIKV become symptomatic. The incubation period is typically 3-7 days (range, 1-12 days). The disease is most often characterized by acute onset of fever (typically >39° C.) and polyarthralgia. Joint symptoms can be severe and debilitating. Other symptoms may include headache, myalgia, arthritis, conjunctivitis, nausea/vomiting, or maculopapular rash. Clinical laboratory findings can include lymphopenia, thrombocytopenia, elevated creatinine, and elevated hepatic transaminases. Acute symptoms typically resolve within 7-10 days. Rare complications include uveitis, retinitis, myocarditis, hepatitis, nephritis, bullous skin lesions, hemorrhage, meningoencephalitis, myelitis, Guillain-Barré syndrome, and cranial nerve palsies. Zika virus, Dengue and chikungunya viruses are transmitted by the same mosquitoes and have similar clinical features. The viruses can circulate in the same area and can cause occasional co-infections in the same patient. Chikungunya virus infection is more likely to cause high fever, severe arthralgia, arthritis, rash, and lymphopenia, while dengue virus infection is more likely to cause neutropenia, thrombocytopenia, hemorrhage, shock, and death. It is important to differentiate viral infections because proper clinical management of can improve outcome.

Dengue, Zika, and chikungunya viruses co-circulate in the Americas. Puerto Rico has experienced eight major epidemics of these diseases in the last 12 years. In the past year, more than 90 thousand tests have been run in Puerto Rico in order to screen pregnant women for recent Zika infections, or diagnose Zika-suspected patients. Diagnostic tests for dengue and chikungunya are also conducted routinely given the similarities of these co-endemic diseases. The arrival of Zika in the Americas is a problem in because it generates cross reactivity with dengue in conventionally available flavivirus diagnostic tests.

Accordingly, there is a need for more efficient, improved, and more sensitive diagnostic tests that can distinguish between closely related infectious agents and/or test for multiple infectious agents at once. For example, there is a strong need for diagnostic tests that provide more definitive identification of the infecting virus (e.g., Zika versus Dengue). Additionally, there is need for more efficient, improved, and more sensitive diagnostic tests that can be used to distinguish between various potential infectious agents in test subject samples where a test subject presents with symptomology common to several potential infective agents and/or the test subject has been exposed to one or more potential infective agents.

BRIEF SUMMARY

The present invention relates to immunoassay compositions and methods that involve the expanded use of test antigens as cross-reactive control antigens (CCAs) to detect and distinguish between multiple infective agents. Because signal results for test antigens described herein can be used to indicate not only the presence or absence of a particular target in a test subject sample, but also illuminate the likelihood of cross-reactivity of a test subject sample across multiple test antigens, the present invention provides a more efficient, improved, and more sensitive compositions and methods for diagnostic tests with multiple test antigens.

In one embodiment the present invention can be advantageously used to not only detect, but to distinguish between, human antibodies to one or more genetically similar infective agents. Thus, the present invention can be used to differentiate between infections caused by such genetically similar infective agents such as, for example, members of the flavivirus genus (Zika, Dengue, West Nile, etc.) or members of the alphavirus genus (chikungunya, etc.). Similar infective agents according to an embodiment of the present invention can be, for example, cross-reactive antigens such as the Zika E protein which is closely related to the E proteins of other flavivirus.

In another embodiment, the present invention may also relate to an efficient immunoassay to detect and distinguish between human antibodies to one or more infective, regardless of whether the infective agents are genetically similar, giving rise to similar symptoms in a subject.

Accordingly, unlike conventionally available diagnostic tests, the present invention provides new in vitro tools, products, and methods that can be used to avoid inaccurate and confusing results stemming from cross-reactivity between infective agents, including genetically similar infective agents, and can aid diagnosis of infection by any one or more specific infective agents. Several virtues of the present invention arise from the new, expanded, and efficient use of infective target antigens to generate both target antigen results and cross-reactive control antigen results within the same assay. That is, the present invention is designed and deployed such that, for each sample, the results obtained for each target antigen may not only indicate infection for that particular target antigen, but also may also be compared to results obtained for a different target antigen and for a normal cell antigen to determine the likelihood of infection for any tested and compared target antigen.

BRIEF DESCRIPTION OF THE DRAWINGS

FIG. 2 depicts an exemplary plate layout for the assay described in Example 4.

FIG. 3A and FIG. 3B depicts an exemplary Zika Interpretation Table.

FIG. 4A, FIG. 4B, and FIG. 4C depict example raw data for a panel of Zika, West Nile, Dengue, Chikungunya and normal serum samples.

FIG. 5A, FIG. 5B, FIG. 5C, FIG. 5D, and FIG. 5E depict similar analyses to that described and depicted with respect to FIG. 4A, FIG. 4B, and FIG. 4C and can be performed using the Dengue, West Nile and Chikungunya antigens to properly categorize these while using an appropriate CCA

DETAILED DESCRIPTION

Figure 1A:
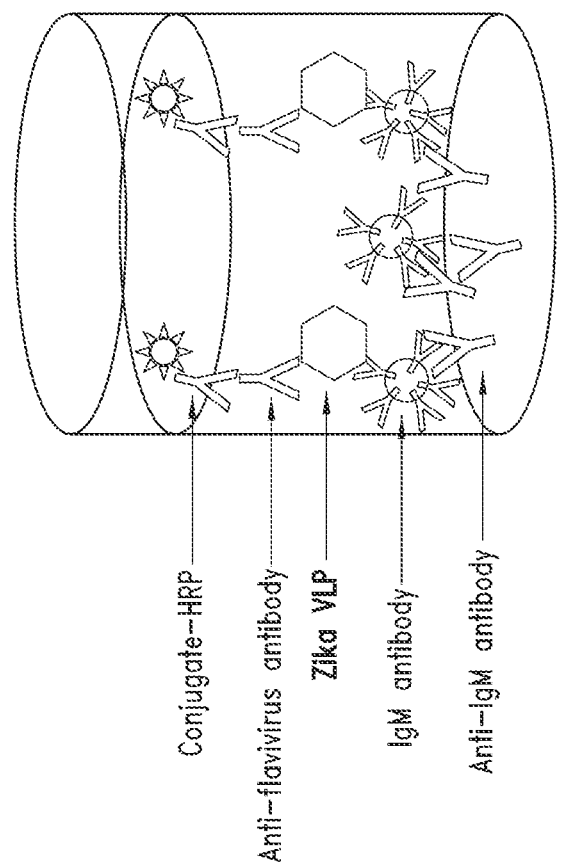
FIG. 1A depicts an ELISA-type assay wherein anti-IgM capture antibodies are immobilized in an assay well, IgM antibodies are bound by the capture antibodies forming antibody-antibody complexes, the antibody-antibody complex is bound to a Zika VLP forming a target-antigen-immune complex, an anti-flavivirus antibody is bound to the Zika VLP, and an HRP-conjugated antibody is bound to the anti-flavivirus antibody.

The present disclosure provides compositions and methods for detecting infection of a subject by an infectious agent, such as a virus. Detection methods include immunoassays that detect antibodies that bind a virus envelope present in a biological sample. Antibodies specific to the virus are determined by assaying against the target virus and against cross-reacting virus or viruses. A subject has been infected with a virus when there are more antibodies to the virus than to the cross-reacting viruses. Kits to perform the immunoassay are also provided.

Definitions

The following terms used in this description are defined below.

Here, any cross-reactivity, concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, cross-reactivity, or structure, unless otherwise indicated.

The term "consisting essentially of" limits the scope of a claim to the specified materials or steps, or to those materials or steps that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. The terms "include," "have" and "comprise" are used synonymously, which terms and variants thereof are intended to be construed as non-limiting.

"Target infectious agent" refers to a pathogen, the presence or absence of which is sought to be determined by a diagnostic assay.

"Common" refers to something that is shared or in common either in whole or in part. For example, the present invention may include common bound components such as test subject sample antibodies that are used to examine reaction with different test antigens. Also, for example, different test antigens may share common reactive or binding sites or portions with each other. Also, for example, the present invention may include a common test antigen conjugate that has common reactive or binding sites or portions with different test antigens.

"Virus-Like Particle" or "VLP" refers to a virus particles made up of one of more viral structural proteins, but lacking the viral genome. Because VLPs lack a viral genome, they are non-infectious. In some embodiments, the VLPs are flavivirus VLPs, such as Zika virus VLPs. In some embodiments, flavivirus VLPs include two flavivirus structural proteins—prM/M and E.

"Cross-reactive control antigen" or "CCA" refers to one or more antigens that are related to the target infectious agent (either by clinical symptom presentation or by sequence homology) and may be used for discerning the relative reactivity levels. In some embodiments, the CCA is a mixture of Dengue and West Nile Virus VLPs. In some embodiments, the CCA is a Zika VLP, a Dengue VLP, or a West Nile VLP. In some embodiments the CCA is a closely related protein common to other viruses. For example, CCA closely related proteins can include the Zika E protein which is closely related to the E proteins of other flavivirus.

"Immunologically challenged" refers to exposure of immune cells in a subject to an infectious agent that results in a humoral immune response. An immunological challenge can result from or during an infection.

"Contacting" or "contacted" refers to placement in direct physical association; includes both in solid and liquid form. "Contacting" is often used interchangeably with "exposed." In some cases, "contacting" refers to incubating a molecule (such as an antibody) with a biological sample.

"Binding agent" refers to a complementary component that has an affinity for its binding pair. An exemplary binding agent is an antibody.

"Antibody" refers to the immunological proteins that are specifically developed (either within the host body or by tissue culture methods) to have an affinity for the target. Exemplary antibodies include IgM, IgG, and IgA isotype antibodies, and fragments thereof.

"Immune complex" refers to a protein complex that comprises an antibody bound to an antigen. In the context of the present disclosure, the term "immune complex" is used to indicate a protein complex that includes an antigen (such as a VLP) bound to at least one antibody. In some cases, the immune complex includes an antigen (such as a VLP) bound to two separate antigen-specific antibodies (each binding a different epitope of the antigen or the same epitope in different regions of the VLP), or includes an antigen (such as a VLP) bound to an antigen-specific antibody, which is further bound to a secondary antibody. The term "antibody-antigen complex" or "antibody-VLP complex" is used to refer to an antigen (or VLP) bound to one antibody. Furthermore, the term "antibody-antibody complex" is used to refer to an antibody bound to a different antibody (such as an antigen-specific antibody bound to a secondary antibody or a capture antibody).

"Antigen-IgM-anti-IgM complex" refers to anti-IgM antibody that pairs with an IgM antibody from the test specimen (e.g., human serum) which in turn is bound to a target antigen. The anti-IgM antibody may be bound. This creates a three-layer binding complex. While IgM antibodies are predominantly discussed herein, the present invention may also include other types of antibodies and proteins.

"Antigen" refers to a protein that is relevant to the target disease. The antigen may either represent the target infectious disease directly or a cross-reactive control infectious disease. In some embodiments, an antigen is a whole virus, viral proteins, or virus like particle.

"Biological sample or sample" refers to a sample obtained from a subject that is tested for the presence of antibodies. Biological samples include, for example, fluid, cell and/or tissue samples. In some embodiments herein, the biological sample is a fluid sample. Fluid sample include, but are not limited to, serum, blood, plasma, urine, feces, saliva, cerebral spinal fluid (CSF), bronchoalveolar lavage fluid, or amniotic fluid.

"Control" refers to a reference standard, for example a positive control or negative control. A positive control is known to provide a positive test result. A negative control is known to provide a negative test result. However, the reference standard can be a theoretical or computed result, for example a result obtained in a population.

"Normal cell antigen" or "NCA" refers to a cell expression system that is identical to the expression system used to generate the target and cross-reactive control antigens with the exception that no antigen is expressed. This may act as the negative control for a specimen and account for any background reactivity that is present within the biological sample.

"Cross-reactive" refers to the immune response that targets homologous portions of closely related diseases (e.g., viruses) that may cause false positive results in serological assays.

"Infectious agent" refers to a pathogen that is capable of infecting a subject. Exemplary infectious agents include Zika virus, Dengue viruses, Chikungunya virus, West Nile virus, or Yellow Fever virus.

"Cross-reacting infectious agent" refers to a disease causing agent that is closely related (highly homologous) to the target infectious disease. In some embodiments, an antigen for a cross-reacting infectious agent can serve as a CCA.

"Homology or homologous" refers to the degree of identity or similarity in both sequence and protein conformation between two (or more) given protein sequences or structures.

"Percent identity" refers to the percentage of amino acid sequence identity when a protein sequence is compared to a related protein sequence. Software, such as National Center for Biotechnology Information BLASTP, may be used to estimate percent identity and homology. Sequence identity/similarity refers to the identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. For example, such nucleic acid or amino acid sequences can include one or more conformational epitopes. In some embodiments, a cross-reactive antigen has at least about 70%, 75%, 80%, 85%, 90%, 95%, 97%, 99%, or 100% sequence identity to a target antigen.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

"Serum" refers to the fluid portion of the blood that separates out from clotted blood. Serum contains many proteins, including antibodies.

"Envelope protein" or "E" protein refers to a flavivirus (including Zika virus) structural protein. The flavivirus E protein is required for membrane fusion, and is the primary antigen inducing protective immunity to flavivirus infection. Flavivirus E protein affects host range, tissue tropism and viral virulence. The flavivirus E protein contains three structural and functional domains, DI-DIII. In mature virus particles the E protein forms head to tail homodimers lying flat and forming a dense lattice on the viral surface.

"Premembrane (prM) protein" refers to a flavivirus structural protein. The prM protein is an approximately 25 kDa protein that is the intracellular precursor for the membrane (M) protein. prM is believed to stabilize the E protein during transport of the immature virion to the cell surface. When the virus exits the infected cell, the prM protein is cleaved to the mature M protein, which is part of the viral envelope (Reviewed in Lindenbach and Rice, In: *Fields Virology*, Knipe and Howley, eds., Lippincott, Williams, and Wilkins, 991-1041, 2001).

"Secondary antibody" refers to an antibody that specifically recognizes a particular isotype of antibody (for example specifically recognizes mouse IgG, human IgG or human IgM). Secondary antibodies for use with the methods disclosed herein include, but are not limited to, anti-mouse IgG, anti-human IgG and anti-human IgM. In some embodiments, the secondary antibody is conjugated to a detectable label, such as a fluorophore, enzyme or radioisotope, to facilitate detection of antibodies and/or immune complexes to which the secondary antibody is bound. In some embodiments the secondary antibody recognizes and Fc region of a particular isotype of antibody.

"Subject or test subject" refers to the individual or organism from which the biological sample is derived. These may include humans, non-human primates, domestic animals, including dogs, cats, horses, and cows, or reservoir species.

"Target antigen" refers to the protein(s) that represents the target infectious disease. These may include envelope proteins, non-structural proteins, viral proteins or VLP.

"Control antigen" refers to the protein(s) that represent either a closely related or symptomatically similar infectious disease. The control antigen may also represent a "normal cell antigen" where no antigen is specifically expressed but this will act as a control for background reactivity. These may include envelope proteins, non-structural proteins, viral proteins or VLP.

"Positive control" refers to a biological specimen that has significant affinity for the target antigen. These may include biological samples or recombinant specimens (for example, chimeric antibodies) that target the infectious disease.

"Negative control" refers to a biological specimen that does not have significant affinity for the target antigen. This is a biological sample that may be used to confirm that the assay was performed properly.

"Detecting reagent" or "detection reagent" refers to the material that specifically binds to the target, cross-reactive or control antigens. This may include a secondary antibody, an avidin complex, a DNA hybrid pair or similar binding partners to specifically indicate the presence of the antigen. The detecting reagent may also incorporate a label (for example, enzymes such as horse radish peroxidase, fluorophores, quantum dots, etc.) that may be used for detection. In addition, separate conjugate partners that interact with the first detecting reagent may be used. For example, conjugate-HRP antibody that specifically interacts with the primary detecting reagent antibody. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as 35S, 11C, 13N, 15O, 18F, 19F, 99mTc, 131I, 3H, 14C, 15N, 90Y, 99Tc, 111In and 125I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

"Immune Status Ratio or ISR" refers to the ratio of the reactivity observed with the target antigen to the reactivity observed with the Control Antigen. That is, ISR=Target Ag $OD_{450}$÷Control Ag $OD_{450}$.

"Cut-off ISR" refers to a threshold level that is experimentally determined, above which a specimen is considered reactive for the target disease. In some embodiments, a cut-off ISR is estimated using receiver operating characterize (ROC) analysis to optimize for sensitivity and specificity. Equal weight may be given to both sensitivity and specificity when performing the analysis.

"Target Ag $OD_{450}$" refers to the raw $OD_{450}$ value obtained with a sample using the target Antigen (e.g., Zika VLP).

"CCA $OD_{450}$" refers to the raw $OD_{450}$ value obtained with a specimen using the Cross-reactive Control Antigen (e.g., VLP).

"NCA $OD_{450}$" refers to the raw $OD_{450}$ value obtained with a specimen using the Normal Cell Antigen (NCA).

"Zika Ag/CCA (Zika ISR)" refers to the ratio of the Zika Ag $OD_{450}$ to the CCA $OD_{450}$. That is, Zika ISR=Zika Ag $OD_{450}$ CCA $OD_{450}$.

"Zika/NCA Ratio" refers to the ratio of the Zika Ag $OD_{450}$ to the NCA $OD_{450}$. That is, Zika Ag $OD_{450}$ NCA $OD_{450}$.

"CCA/NCA Ratio" refers to the ratio of the CCA $OD_{450}$ to the NCA $OD_{450}$. That is, CCA $OD_{450}$ NCA $OD_{450}$.

"ZIKA ISR" refers to the Zika Ag $OD_{450}$ to the CCA $OD_{450}$. That is, ZIKA ISR=Zika Ag $OD_{450}$ CCA $OD_{450}$.

"DENV ISR" refers to the Dengue Ag $OD_{450}$ to the CCA $OD_{450}$. That is, DENV ISR=DENV Ag $OD_{450}$ CCA $OD_{450}$.

The "flavivirus" genus includes, for example, the West Nile virus, dengue virus, tick-borne encephalitis virus, yellow fever virus, Zika virus and several other viruses which may cause encephalitis, as well as insect-specific flaviviruses (ISFs) such as cell fusing agent virus (CFAV), Palm Creek virus (PCV), and Parramatta River virus (PaRV).

The "alphavirus" genus includes, for example, alphaviruses able to infect various vertebrates such as humans, rodents, fish, birds, and larger mammals such as horses as well as invertebrates. Infections caused by members of the alphavirus genus include Chikungunya, Ross River, Sindbis, Barmah Forest, Mayaro and O'nyong-nyong, ad Eastern, Western and Venezuelan Equine Encephalitides, etc.

Additional definitions may be set forth throughout this disclosure.

Methods and compositions for performing diagnostic assays capable of detecting whether a subject has been immunologically challenged by an infectious agent are described herein.

The present invention provides for detection of a humoral immune response directed against a target infectious agent (e.g., Zika virus) while reducing the incidence of false-positive results caused by cross-reactivity with non-target infectious agents that are closely related to the target infectious agent. For example, different Flaviviruses, such as dengue virus, may be cross-reactive with Zika virus due to genetic similarities.

In some embodiments, the present invention comprises contacting anti-IgM binding agents separately with one of a subject's test sample comprising IgM of unknown affinity, a positive control IgM, or a negative control IgM to form a complex of IgM bound by the anti-IgM binding agent (each, separately, a "complex" and, collectively, "complexes"). Here, a single subject test sample would relate to, for example, three (3) distinct complexes, each involving the anti-IgM binding agent and one of IgM from the subject's test sample, the positive control IgM, and the negative control IgM. Each distinct complex is then contacted with a target antigen derived from the target infectious agent, such as a Zika Virus-Like Particle (VLP), or a cross-reactive control antigen (CCA), such as a Dengue VLP. If IgM are present in a test sample that bind the target antigen or the CCA, then the IgM will bind and capture one or more of the antigens. In some embodiments, the complex is contacted with a normal cell antigen (NCA) control that contains no antigen that binds the positive control or negative control IgM. A detection reagent that recognizes the antigens (e.g., the Zika VLP and the CCA VLP) is then contacted with the complex to detect whether IgM captured the target antigen or CCA. One exemplary detection reagent is a pan-flavivirus anti-VLP antibody conjugated to horseradish peroxidase, but other detection reagents may also be used. The amount of bound detection reagent is then quantified using any number of methods known in the art including, for example, detection of colorimetric change, fluorescence, or radiation.

The methods disclosed herein reduce the false-positive results by comparing the amount of captured target antigen (e.g., Zika VLP) to the amount of captured CCA (e.g., dengue VLP) to generate a ratio referred to as an immune status ratio (ISR). If the ISR is above an experimentally determined threshold, then the test sample is positive for IgM that are specific for the target antigen; thus, indicating that the subject has been immunologically challenged with the target infectious agent. If the ISR is below an experimentally determined threshold, then the test sample is negative for IgM specific to the target antigen; thus, indicating that the subject has not been immunologically challenged with the target infectious agent.

In some embodiments, the method comprises using two or more target antigens and each antigen will dually serve as a target antigen and an individual cross-reacting antigen control.

In an example, involving a test for dengue, Zika, and chikungunya, the dengue antigen can serve as the CCA an anti-Zika IgM ELISA, the Zika antigen can serve as the CCA for an anti-dengue IgM ELISA, and the chikungunya antigen can serve as an NCA control for both Zika and dengue ELISAs while the dengue or Zika antigen will serve as the normal control antigen for the anti-chikungunya IgM ELISA. Advantageously, the throughput of testing of such a test is increased because the assay can be formatted to allow simultaneous testing of multiple patients (e.g., 28 patients) for dengue, Zika, and chikungunya in a single plate.

In one embodiment, the present invention has claims directed to a method for detecting antibody to a target virus in a subject, comprising: contacting a biological sample obtained from a subject with anti-IgM antibody to form an IgM-anti IgM complex; contacting an antigen from the target virus or a cross-reactive control antigen (CCA) from a related virus with the complex; incubating for a time sufficient to allow binding of the antigen to the complex to form an antigen-IgM-anti-IgM complex; contacting the antigen-IgM-anti-IgM complex with a reagent that binds to both the target virus antigen and the CCA; and detecting the bound reagent; wherein a ratio of detected reagent for target virus antigen to detected reagent for CCA of greater than a minimum value indicates presence of antibody to the target virus.

In one embodiment, the target virus and cross-reactive control virus are Flaviviruses. In other embodiments, the target virus and cross-reactive control virus are alphaviruses.

In an aspect, the claims are directed to a method for detecting antibody to Zika virus in a subject, comprising: contacting a biological sample obtained from a subject with anti-IgM antibody to form an IgM-anti IgM complex; contacting a Zika antigen or a cross-reactive control antigen (CCA) with the complex; incubating for a time sufficient to allow binding of the antigen to the complex to form an antigen-IgM-anti-IgM complex; contacting the antigen-IgM-anti-IgM complex with a reagent that binds to both the Zika antigen and the CCA; and detecting the bound reagent; wherein a ratio of detected reagent for Zika antigen to detected reagent for CCA greater than a minimum threshold value indicates presence of antibody to Zika virus. In some embodiments, the CCA is either Dengue virus antigen or West Nile virus antigen or a combination of Dengue virus antigen and West Nile virus antigen. In some embodiments, the Zika antigen, Dengue virus antigen, and West Nile virus antigen is a virus-like particle (VLP).

In certain embodiments, the reagent is an antibody. In some embodiments, the antibody is labeled. In other embodiments, the ratio of greater than about 1.7 indicates presence of antibody to Zika virus. Generally, the biological sample is serum, but it is not necessarily so.

In another aspect, the claims provide a method of detecting antibody to a flavivirus other than Zika virus in a subject, comprising: contacting a biological sample obtained from a subject with anti-IgM antibody to form an IgM-anti IgM complex; contacting a Zika antigen or a cross-reactive control antigen (CCA) or a normal cell antigen (NCA) with the complex; incubating for a time sufficient to allow binding of the antigen to the complex to form an antigen-IgM-anti-IgM complex; contacting a reagent that binds to both the Zika antigen and the CCA; and detecting the bound reagent; wherein a ratio of detected reagent for Zika antigen to detected reagent for CCA is less than about 1.5 and a ratio of detected reagent for either Zika antigen or CCA to detected reagent for NCA is greater than about 1.5 indicates presence of antibody to flavivirus other than Zika virus.

In embodiments, the CCA is a combination of Dengue virus antigen and West Nile virus antigen. In embodiments, the Zika antigen, Dengue virus antigen, and West Nile virus antigen is a virus-like particle (VLP).

In certain embodiments, the reagent is an antibody, and at times is labeled. In embodiments, the biological sample is serum.

The present invention also provides for a kit for detecting antibody to Zika virus in a subject, comprising: a Zika antigen and a CCA; a reagent that binds to both Zika antigen and CCA. The kit may comprise anti-IgM antibody.

In one aspect, the claims provide a composition comprising Zika antigen, and in embodiments, the Zika antigen is a VLP. In another aspect, the composition comprises CCA. In some embodiments, the CCA is either Dengue virus antigen or West Nile virus antigen or a mixture of Dengue virus antigen and West Nile Virus antigen. In some embodiments, the Dengue virus antigen and the West Nile Virus antigen is a VLP.

These and other aspects of the present invention will become evident upon reference to the following detailed description and attached drawings.

Infectious Agents

Some infectious agents, such as viruses, are members of a genus that contains organisms with closely-related envelopes, coats, outer membranes, etc. As a result, antibodies in subjects infected by a particular infectious agent may cross-react with other members of the genus.

Without wishing to be bound by theory, cross-reactivity can be due to similar amino acid sequences or carbohydrate structures on proteins. Examples of infectious agents that raise cross-reacting antibodies that may confound diagnosis include (but are not limited to) members of Flaviviruses, alphaviruses, Burkholderia pseudomallei, influenza A, and influenza B. Cross-reactivity makes it difficult to use immunoassays to diagnose infection by a particular agent. Within each genus the cross-reactivity can be significant (e.g., different flaviviruses can generate cross-reactive antibodies such as Zika and West Nile). Also, different alphaviruses can cause cross-reacting antibodies with one another, etc. But antibodies generated to a flavivirus are not expected to be likely to cross-react with an alphavirus.

flavivirus is a genus of viruses whose members includes the West Nile virus, dengue virus, tick-borne encephalitis virus, yellow fever virus, Zika virus, Japanese encephalitis virus and several other viruses which may cause encephalitis. The genus of alphaviruses also contains many pathogenic species, including Chikungunya virus, Ross River virus, Semliki Forest virus, Venezuelan equine encephalitis virus, and Western equine encephalitis virus. Especially because Zika virus causes microcephaly, a birth defect where the newborn's head is smaller than normal and is linked with serious developmental problems, diagnosis of Zika virus infection is critical. Antibodies to Zika virus can cross-react with other Flaviviruses, many of which overlap in geographical range.

Many pathogens result in similar clinical presentation and symptoms. Accordingly, some embodiments of the instant disclosure provide methods for distinguishing between pathogens with similar symptoms or cross-relative structural proteins.

In the methods and compositions described herein, the target infectious agent and one or more cross-reacting infectious agents are used as reagents. In the case of viruses, the reagents can be e.g., whole virus, typically inactivated, isolated envelope protein or proteins, or envelope protein(s) displayed on the surface of a carrier. The envelope protein(s) can be isolated from virus or produced by recombinant techniques, which are well-known. Suitable carriers include beads, yeast, bacteria, other viruses, virus-like particles, etc. Generally, the nucleotide sequence encoding the membrane protein(s) or the most immunogenic protein is expressed from an expression vector. Methods and suitable expression vectors and hosts are well known.

The Zika virus, or "ZIKV," is a flavivirus and contains a single, positive sense viral RNA of 10.7 kb in-length that translates into a single poly-protein, which is subsequently cleaved into three structural proteins (capsid, premembrane/membrane, envelope; C, prM/M, E) and seven non-structural proteins (NS1, NS2A, NS2B, NS3, NS4A, NS4B, and NS5) (Kuno and Chang, *Arch Virol* 152, 687-696, 2007). It has been previously demonstrated with other Flaviviruses that expression of prM and E glycoproteins alone can self-assemble and be secreted as immunogenic virus-like particles (VLPs) (Chang et al., *J Virol* 74, 4244-4252, 2000; Davis et al., *J Virol* 75, 4040-4047, 2001; Chang et al., *Virology* 306, 170-180, 2003; Konishi et al., *J Virol* 72, 4925-4930, 1998; Konishi et al., *Vaccine* 21, 3713-3720, 2003), all of which are incorporated by reference in entirety. In addition, VLPs of several non-ZIKV Flaviviruses have been previously generated (Chang et al., *J Virol* 74, 4244-4252, 2000; Davis et al., *J Virol* 75, 4040-4047, 2001; Hunt et al., *J Virol* Methods 97, 133-149, 2001), all of which are incorporated by reference in entirety.

An exemplary reagent is a virus-like particle (VLP) that displays the envelope protein of a virus. Virus-like particles (VLPs) are shell-like viruses that lack virus-specific genetic materials. The expression of viral structural proteins can self-assemble into a VLP. VLPs may be produced in a variety of host cells, such as in insect cells, human cells, plants, and yeast. The choice of an expression vector depends in part upon the host cell for production. Vectors and host cells are well known.

Methods of producing VLPs are known in the art and described in Chang G J et al. *Virology.* 2003; 306(1):170-80; Purdy DE & Chang G J. *Virology.* 2005; 333(2):239-50; Schalich J, et al. *Journal of Virology.* 1996; 70(7):4549-57; Allison S L, et al. *Journal of Virology.* 1995; 69(9):5816-20; Allison S L, et al. *Journal of Virology.* 2003; 77(21):11357-66, which are incorporated by reference herein in entirety.

In some embodiments, the target virus and CCA virus VLPs express the relevant prM and E (envelope) proteins. The prM proteins are cleaved and the E proteins are displayed on the VLP surface. In certain embodiments, the VLPs display E proteins and are produced in mammalian cells. The coding sequence for prM and E are amplified from the viral genome and inserted into a plasmid vector. Expression is under control of the cytomegalovirus early gene promoter and transcriptional control element and an engineered Japanese Encephalitis virus (JEV) signal sequence element is in-frame with the prM/E sequence. Other promoters and signal sequences may be used alternatively. The plasmid is transfected into mammalian cells, and the VLPs collected from cell supernatant. VLPs may be isolated and concentrated using standard techniques and methods.

In some embodiments, the target antigen or the CCA can comprise a non-structural viral protein. For example, the target antigen can comprise NS1, NS2A, NS2B, NS3, NS4A, NS4B, NS5, or any combination thereof. In some embodiments, the target antigen can comprise a C protein. In some embodiments, the target antigen or the CCA is a VLP. The VLP can comprise E, M, C, NS1, NS2A, NS2B, NS3, NS4A, NS4B, NS5, or any combination thereof.

In some embodiments, the target and CCA virus antigens are the envelope protein that is produced by recombinant technology. The envelope protein can be the precursor form or the mature, processed form. In some embodiments, the target virus antigen can be recombinant and the CCA virus antigen can be a VLP, or vice versa. Usually the target and CCA antigens will both be the same type of antigen (e.g., VLP, recombinant envelope, isolated protein, inactivated virus).

In some embodiments, an antigen is produced that comprises at least one CHIKV protein. The CHIKV antigen can comprise E1, E2, or a combination thereof. In some embodiments, the CHIKV antigen is a VLP.

Immunoassays

A variety of immunoassays are suitable for determining infection of a subject by an infectious agent, such as a Flavivirus. Immunoassays are well known by those of ordinary skill. In a typical immunoassay the target antigen and control antigen (negative control) are contacted with a biological sample from a test subject. A subject can be any species that is susceptible to infection by the infectious agent, and most typically is human. The sample is usually blood or a component of blood that contains antibodies, typically serum. Alternatively, the sample can be a tissue, such as a lymph node or bone marrow. Negative and positive control sera are generally included in an immunoassay. After unbound reagents are washed away, the bound antigen-antibody complex is detected and usually quantified. A detection system can be a labeled antibody to the antigen or to immunoglobulins in the subject's sample. Many different suitable labels can be used, including radioactive labels, enzymatic labels that react with a visualizable substrate (e.g., a chromogenic substrate). The assay can be performed in any medium, including in liquid or on a solid substrate.

The solid support may be any solid material known to those of ordinary skill in the art to which the antibody may be attached. For example, the solid support may be a test well in a microtiter plate, or a nitrocellulose or other suitable membrane. Alternatively, the support may be a bead or disc formed of glass, fiberglass, latex or a plastic material such as polystyrene or polyvinylchloride. The support may also be a magnetic particle or a fiber optic sensor, such as those disclosed, for example, in U.S. Pat. No. 5,359,681.

A convenient format of an immunoassay is an ELISA. The immunoassay can detect IgM, IgG, or IgA antibodies to the target. The presence of IgM antibodies usually signals a recent infection. In an embodiment of the present invention, the ZIKV IgM Capture ELISA described herein is an enzyme linked capture immunoassay for the detection of human IgM antibodies targeting the ZIKV envelope glycoproteins. Polystyrene microtiter wells are pre-coated with capture antibodies (anti-IgM) for human IgM. When IgG antibodies are to be detected, then the capture antibody will be an anti-IgG (that is reactive to all sub-classes) or anti-IgG subclass antibody. It is also suitable to use a non-antibody capture reagent that binds IgM, IgG, or IgA antibodies. For example, *Staphylococcus* protein A binds human IgG antibodies.

Positive control (serum that is known to have IgM antibodies to the infectious agent Zika virus), negative control (serum that is known to not have IgM antibodies to the infectious agent Zika virus), and unknown test samples are diluted into a sample dilution buffer and then added to the ELISA plate in appropriate concentrations. Following removal of unbound serum components, VLPs of the target agent (e.g., Zika virus) and a mixture of one or more cross-reactive agents are added to separate wells. A normal cell control composition (supernatant from host cells that do not produce VLPs) may be added to separate wells as an internal control and to assist in detecting antibodies to related, non-target agents. After removal of unbound VLPs, the amount of bound VLPs is determined. The detecting reagent can be directly observable or indirectly observable. For example, the detecting reagent can be an antibody that binds a conserved sequence in the target and cross-reacting VLPs. The antibody can be labeled with a directly detectable label, such as a radioactive label or a fluorescent label. Or the label can be indirectly detectable, such as an enzyme that acts on a chromogenic substrate that is separately added to the wells. Many directly detectable labels and indirectly detectable labels are well-known.

In some embodiments, the method includes contacting a biological sample having antibodies with a target antigen under conditions sufficient to form a target antigen-antibody complex if antibodies that bind the target antigen are present in the sample; contacting the sample with a cross-reactive control antigen (CCA) under conditions sufficient to form a CCA-antibody complex if antibodies that cross-react or bind the CCA are present in the sample; and detecting the target antigen-antibody complexes and CCA-antibody complexes. In some embodiments, the method further comprises contacting the sample with a normal cell antigen (NCA) under control conditions that are the same as conditions sufficient to form the target antigen-antibody complex and the CCA-antibody complex and detecting NCA-antibody complexes. The detection of NCA-antibody complexes serves as control for background levels of antigen-antibody complex formation. The target antigen-antibody complexes and the CCA-antibody complexes are collectively referred to as antigen-antibody complexes.

In some embodiments, the method includes contacting the sample with an anti-antibody binding agent. The anti-antibody binding agent can be immobilized on a solid support. The anti-antibody binding agent can be in a liquid medium. In some embodiments, the anti-antibody binding agent is a capture antibody. In an alternative embodiment, the anti-antibody binding agent is a detection antibody. The anti-antibody binding agent can be an anti-IgM, anti-IgG, or anti-IgA antibody. In some embodiments, an anti-IgG antibody is an anti-IgG that is reactive to all sub-classes or anti-IgG subclass antibody. Exemplary anti-antibody reagents *Staphylococcus* protein A binds human IgG antibodies.

In some embodiments, detecting the antigen-antibody complexes includes contacting the antigen-antibody complexes with a detection reagent that binds the target-antigen and the CCA. In some embodiments, the detection reagent is an antibody. The antibody can be a pan-flavivirus antibody that binds to more than one Flavivirus. In some embodiments, the pan-flavivirus antibody binds to Zika virus, dengue virus, West Nile virus, yellow fever virus, Japanese encephalitis virus, or any combination thereof. In some embodiments, the pan-flavivirus antibody binds to Zika virus and Dengue virus. In some embodiments, the pan-flavivirus antibody binds to Zika virus, Dengue virus, and West Nile virus. In some embodiments, the detection reagent comprises a detectable label. In some examples, detecting the antigen-antibody complexes comprises contacting the antigen-antibody complexes with a detection reagent and contacting detection antibody with a secondary antibody that binds the detection reagent. In some embodiments, the secondary antibody comprises a detectable label.

In certain embodiments, the secondary antibody is an anti-IgM antibody or an anti-IgG, such as anti-human IgM antibody or an anti-human IgG antibody.

Accordingly, in some embodiments, the method includes providing a capture antibody bound to a solid support; contacting the capture antibody with the biological sample having antibodies and suspected of having an infection under conditions sufficient to allow binding of the capture antibody to antibodies present in the biological sample, thereby forming antibody-antibody complexes; contacting a portion of the antibody-antibody complexes with a target antigen under conditions sufficient for the target antigen to bind the anti-target-antigen antibodies present in the biological sample, thereby forming target-antigen-immune complexes; contacting a portion of the antibody-antibody complexes with a CCA under conditions sufficient for the CCA to bind the anti-target-antigen antibodies present in the biological sample, thereby forming CCA-immune complexes; contacting a portion of the antibody-antibody complexes with an NCA under conditions sufficient for the NCA to bind the anti-target-antigen antibodies present in the biological sample, thereby forming NCA-immune complexes; and detecting the presence of the immune complexes.

In some embodiments, the target-antigen is a Zika VLP and the CCA is a non-Zika flavivirus VLP, such as a Dengue VLP or a West Nile VLP. In some embodiments, the target antigen is a Dengue VLP, and the CCA is a non-Dengue flavivirus VLP, such as a Zika VLP or a West Nile VLP. In some embodiments, the target antigen is a West Nile VLP, and the CCA is a non-West Nile flavivirus VLP, such as a Zika VLP or a Dengue VLP. In some embodiments, the NCA is a sample generated from cells that do not produce a flavivirus VLP. In some embodiments, the NCA comprises a cellular control that lacks expression of a VLP. In some embodiments, the NCA comprises an alphavirus VLP. In some embodiments, the NCA comprises a CHIKV VLP.

In some embodiments, the method includes providing an anti-IgM antibody bound to a solid support; contacting the anti-IgM antibody-bound solid support with a biological sample having IgM antibodies and suspected of having a ZIKV infection under conditions sufficient to form anti-IgM-antibody-IgM complexes; contacting a portion of the anti-IgM-antibody-IgM complexes with a ZIKV VLP under conditions sufficient for the ZIKV VLP to bind anti-ZIKV-antibodies or cross-reactive antibodies from the biological sample to form antibody-ZIKV VLP immune complexes; contacting a portion of the anti-IgM-antibody-IgM complexes with a Dengue VLP under conditions sufficient for the Dengue VLP to bind anti-Dengue-antibodies or cross-reactive antibodies from the biological sample to form antibody-Dengue VLP immune complexes; and contacting a portion of the anti-IgM-antibody-IgM complexes with a CHIK VLP under conditions sufficient for the CHIK VLP to bind anti-CHIK VLP-antibodies from the biological sample to form antibody-CHIK VLP immune complexes; and detecting the presence of the immune complexes.

Detecting the presence of the immune complexes may include contacting the immune complexes with an antibody that specifically binds the VLP and comprises a detectable label.

In some embodiments, the secondary antibody is an anti-IgM antibody, such as anti-human IgM antibody. In other embodiments, the secondary antibody is an anti-IgG antibody, such as anti-human IgG antibody.

In some embodiments of the methods of detecting ZIKV-specific antibodies, the biological sample is a biological fluid sample. In some examples, the biological fluid sample comprises serum, blood or plasma. In particular embodiments, the biological sample comprises serum.

In certain embodiments, horse radish peroxidase (HRP) is conjugated to the anti-VLP, e.g., antibodies to cross-reactive E protein, and the conjugate is added to each well. For example, in this embodiment, an anti-flavivirus antibody cross-reacts with West Nile, Zika, Dengue, etc. and is directly labeled to HRP. In an embodiment, HRP conjugated antibodies can be directly used to detect differential presence of M/E reactive antibodies, or can be done indirectly by the use of anti-mouse or other species specific antibody conjugate. In another embodiment, a primary antibody may be unlabeled and a secondary antibody (e.g., HRP labeled anti-mouse IgG HRP) can be used for detection.

After washing, wells are incubated with a tetramethylbenzidine (TMB) substrate. An acidic stop solution is then added and the degree of enzymatic turnover is determined by the absorbance (optical density) measurement at 450 nanometers. If human IgM antibodies targeting the ZIKV envelope glycoproteins are present, a complex is formed consisting of the IgM, antigen, and conjugate. If IgM antibodies targeting the ZIKV envelope glycoproteins are not present, then the antigen and conjugate are washed away. A sample is deemed positive (having IgM antibodies) for the infectious agent when the detectable signal is higher for the infectious agent than for the cross-reacting agents.

In certain embodiments, the methods provide for distinguishing the presence of antibodies that bind a target infectious agent from antibodies that cross-react with cross-reactive agent. For example, the methods allow for the detection of anti-ZIKV antibodies, while distinguishing the positive result from cross-reaction with antibodies that bind, for example, Dengue virus or West Nile virus. In some embodiments, the methods allow for distinguishing between viral infections that have similar symptoms or clinical presentation. For example, the methods can distinguish between one or more flaviviruses and Chikungunya virus in the same assay.

An exemplary way to calculate the relative amounts of IgM antibodies to the target agent and the cross-reactive agent is disclosed in the Examples. Briefly, the value of the detectable signal for the target agent is divided by the value for the cross-reactive agent. This is called the target ISR.

In one embodiment, for a sample to be considered as having specific IgM antibodies to the target agent, the ISR is greater than or equal to 1.1, or greater than or equal to 1.2, or greater than or equal to 1.3, or greater than or equal to 1.4, or greater than or equal to 1.5, or greater than or equal to 1.6, or greater than or equal to 1.7, or greater than or equal to 1.8, or greater than or equal to 1.9, or greater than or equal to 2.0. In this embodiment, generally, the cut-off ISR is greater than or equal to 1.7 or 1.8. The cut-off value may be experimentally determined and typically is chosen to minimize false positives and negatives. Similarly, for samples with target ISR values less than the cut-off for positive reactivity or more usually with an ISR of about 1.0, a cross-reactive ISR is calculated by dividing the value of the signal for the cross-reactive agent by the value for the normal cell antigen. If this ISR is greater than or equal to 1.1, or greater than or equal to 1.2, or greater than or equal to 1.3, or greater than or equal to 1.4, or greater than or equal to 1.5, or greater than or equal to 1.6, or greater than or equal to 1.7, or greater than or equal to 1.8, or greater than or equal to 1.9, or greater than or equal to 2.0, then the sample has IgM antibodies to the cross-reactive agent(s). In this embodiment, generally, the cut-off ISR is greater than or equal to 1.7 or 1.8.

In some embodiments, the method comprises detecting and differentiating between infections with different Flaviviruses (e.g., ZIKV, DENV, WNV). For example, the value of the detectable signal for the target agent is divided by the value for the cross-reactive agent to produce the target ISR value. In some embodiments, the target agent is ZIKV and the cross-reactive agent is DENV or WNV. In some embodiments, the target agent is DENV and the cross-reactive agent is ZIKV or WNV. In some embodiments, the target agent is WNV and the cross-reactive agent is DENV or ZIKV. A target ISR that is greater than the cut-off value indicates that the sample comprises antibodies specific for the target agent. The cut-off ISR may be experimentally determined and typically is chosen to minimize false positives and negatives. For example, a target ISR greater than or equal to 1.8 in that the sample is reactive for the target antigen. A target ISR between 1.8 and 1.6 indicates that the sample should be retested. A target ISR less than or equal to 1.6 indicates that an NCA analysis should be performed. The NCA analysis includes generating a Target antigen/NCA value by dividing the target antigen detectable signal for the target agent by the detectable signal for the NCA. Further, a CCA/NCA value is generated by dividing the detectable signal for the CCA by the detectable signal for the NCA. If, for example, the Target antigen/NCA value is greater than or equal to 1.7 and the CCA/NCA value is greater than or equal to 1.7, then the results indicate that the sample is possibly reactive to the target antigen and possibly reactive to the CCA. If, for example, the Target antigen/NCA value is greater than or equal to 1.7 and the CCA/NCA value is less than or equal to 1.7, then the results indicate that the sample is reactive to the target antigen. If, for example, the Target antigen/NCA value is less than or equal to 1.7 and the CCA/NCA value is greater than or equal to 1.7, then the results indicate that the sample is reactive to the CCA antigen. If, for example, the Target antigen/NCA value is less than or equal to 1.7 and the CCA/NCA value is less than or equal to 1.7, then the results indicate that the sample is not reactive to the target antigen and not reactive to the CCA.

In some embodiments, the NCA sample comprises a CHIKV antigen (e.g., VLP). If the detectable signal from the NCA-CHIKV antigen is at least three times higher than the detectable signal from target antigen (e.g., ZIKV) and the CCA (e.g., DENV), then the results indicate that the sample is reactive with the NCA-CHIKV antigen.

Kits

The present disclosure provides kits for performing the assays disclosed herein. For a solid-support ELISA assay, the kit comprises the target antigen, e.g., ZIKV antigen or VLP (Zika Ag) that comprises the Zika envelope glycoproteins; the Normal Cell Antigen (NCA), and optionally, the Cross-reactive Control Antigen that comprises one or more cross-reactive control antigens or VLP (CCA).

In one embodiment, all or substantially all of test components and buffers for the different test antigens to be used as CCAs are substantially the same.

In some embodiments, the kit comprises a ZIKV antigen or VLP that comprises ZIKV envelope glycoproteins; a DENV antigen or VLP that comprises DENV envelope glycoproteins, and an NCA. In some embodiments, the kit comprises a ZIKV antigen or VLP that comprises ZIKV envelope glycoproteins; a WNV antigen or VLP that comprises WNV envelope glycoproteins, and an NCA. In some embodiments, the kit comprises a ZIKV antigen or VLP that comprises ZIKV envelope glycoproteins; a WNV antigen or VLP that comprises WNV envelope glycoproteins, a DENV antigen or VLP that comprises DENV envelope glycoproteins, and an NCA. In some embodiments, the NCA comprises a CHIKV antigen or VLP.

Other components that may be included in the kit are: microtiter test strips or plate that is coated with anti-IgM antibodies or the anti-IgM antibodies (not coated onto a solid support); a negative control sample, a positive control sample, a detecting agent and substrate if used with the detecting agent, dilution buffers, wash buffers, stop solution, and instructions.

Additional Embodiments

In one embodiment, the present invention relates to a method for detecting antibody to a target virus in a subject, comprising: (a) contacting a biological sample obtained from a subject with anti-IgM antibody to form an IgM-anti IgM complex; (b) contacting an antigen from the target virus or a cross-reactive control antigen (CCA) from related viruses with the complex; (c) incubating for a time sufficient to allow binding of the antigen to the complex to form an antigen-IgM-anti-IgM complex; (d) contacting the antigen-IgM-anti-IgM complex with a reagent that binds to both the target virus antigen and the CCA; and (e) detecting the bound reagent; wherein a ratio of detected reagent for target virus antigen to detected reagent for CCA of greater than a minimum value indicates presence of antibody to the target virus. In this embodiment, the target virus and cross-reactive control virus(es) may be Flaviviruses. Also in this embodiment, the target virus and cross-reactive control virus(es) may be alphaviruses.

In another embodiment, the present invention comprises a method for detecting antibody to Zika virus in a subject, comprising: (a) contacting a biological sample obtained from a subject with anti-IgM antibody to form an IgM-anti IgM complex; (b) contacting a Zika antigen or a cross-reactive control antigen (CCA) with the complex; (c) incubating for a time sufficient to allow binding of the antigen to the complex to form an antigen-IgM-anti-IgM complex; (d) contacting the antigen-IgM-anti-IgM complex with a reagent that binds to both the Zika antigen and the CCA; and (e) detecting the bound reagent; wherein a ratio of detected reagent for Zika antigen to detected reagent for CCA of greater than a minimum value indicates presence of antibody to Zika virus. In this embodiment, the CCA may be either Dengue virus antigen or West Nile virus antigen or both Dengue virus antigen and West Nile virus antigen. Also in this embodiment, the Zika antigen, Dengue virus antigen, and West Nile virus antigen may be a virus-like particle (VLP). Also in this embodiment, the reagent may be an antibody that may or may not be labeled. Also in this embodiment, the minimum value may be 1.5, 1.6, 1.7, or 1.8 or another experimentally determined ratio. Also in this embodiment, the biological sample may be serum or plasma.

In one embodiment the present invention is a method of detecting antibody to a flavivirus other than Zika virus in a subject, comprising: (a) contacting a biological sample obtained from a subject with anti-IgM antibody to form an IgM-anti IgM complex; (b) contacting a Zika antigen or a cross-reactive control antigen (CCA) or a normal cell antigen (NCA) with the complex; (c) incubating for a time sufficient to allow binding of the antigen to the complex to form an antigen-IgM-anti-IgM complex; (d) contacting a reagent that binds to both the Zika antigen and the CCA; and (e) detecting the bound reagent; wherein a ratio of detected reagent for Zika antigen to detected reagent for NCA is less than an established value and a ratio of detected reagent for CCA to detected reagent for NCA is greater than the established value indicates presence of antibody to flavivirus other than Zika virus. In this embodiment, the CCA may be either Dengue virus antigen or West Nile virus antigen or a combination of Dengue virus antigen and West Nile virus antigen. Also in this embodiment, the Zika antigen, Dengue virus antigen, and West Nile virus antigen may be virus-like particles (VLP). Also in this embodiment, the minimum value may be 1.5, 1.6, 1.7, or 1.8 or another experimentally determined ratio. Also in this embodiment, the reagent may be an antibody and may or may not be labeled. Also in this embodiment, the biological sample may be serum or plasma.

In another embodiment, the present invention relates to a kit for detecting antibody to Zika virus in a subject, comprising: (a) a Zika antigen and a CCA; and (b) a reagent that binds to both Zika antigen and CCA. In this embodiment, the kit may further comprise an anti-IgM antibody.

In another embodiment, the present invention relates to a composition comprising Zika antigen that may or may not be a VLP.

In another embodiment, the present invention relates to a composition comprising a CCA. In this embodiment the CCA may or may not be a mixture of Dengue virus antigen and West Nile Virus antigen. Also in this embodiment, any Dengue virus antigen and West Nile Virus antigen may or may not be a VLP.

In another embodiment, the present invention is a method for detecting antibody to a target infectious agent in a subject, comprising: (a) contacting a biological sample obtained from a subject with a reagent that binds to antibody to form an antibody-reagent complex; (b) contacting an antigen from the target infectious agent or a cross-reactive control antigen (CCA) from a related infectious agent with the complex; (c) incubating for a time sufficient to allow binding of the antigen to the complex to form an antigen-antibody-reagent complex; (d) contacting the antigen-antibody-reagent complex with a second reagent that binds to both the target antigen and the CCA antigen; and (e) detecting the bound second reagent; wherein a ratio of detected second reagent for target antigen to detected second reagent for CCA of greater than a minimum value indicates presence of antibody to the target infectious agent. In this embodiment, the antibody may be IgM, IgG, or IgA. In this embodiment, the infectious agent is a virus.

In one embodiment, the present invention is a diagnostic assay comprising different test antigens, wherein each test antigen binds to each of a common bound component and a common test antigen conjugate. In this embodiment, the different test antigens provide for an expanded use of test antigens as cross-reactive control antigens (CCAs). Accordingly, the diagnostic test compositions and methods described herein advantageously provide for test antigen and additional test antigen CCA related signaling across, for example, different test sample wells. Here, the common bound component may be, for example, the antibody or protein of interest from a subject sample. Here, the bound component may be immobilized, for example, in or on a surface of a well or together with or on the surface of a bead.

In an embodiment, the common test antigen conjugate may be an antibody or a protein, or may be a mixture of one or more antibodies or of one or more proteins, or a combination of one or more antibodies or proteins.

In an embodiment, each of the different test antigens indicates the presence (by binding) of absence (by not binding) of a particular bound component and also indicates the likelihood of cross-reactivity error relative to at least one other different test antigen. Each of the different test antigens may separately and may simultaneously indicate the presence of absence of a particular bound component and also indicate the likelihood of cross-reactivity error relative to at least one other different test antigen.

In an embodiment, the diagnostic test assay includes different test antigens sharing a common genetic heritage or genetic similarity. For example, the different test antigens may be members of the same viral genus, such as members of the flavivirus genus or the alphavirus genus. Also, the different test antigens may include components common, or shared, by or across members of the same viral genus, such as certain envelop proteins, etc. Such commonality allows for the use of the different test antigens as CCAs. In one embodiment, CCAs may be highly homologous or share a sequence that has at least about 70%, 75%, 80%, 85%, 90%, 95%, 97%, 99%, or 100% sequence identity to a target antigen.

The present invention may also relate to a method for distinguishing between related infective agents in vitro comprising: at least two different test antigens; and a common cross-reactive test antigen conjugate. In one embodiment, the method requires formation of a complex including at least one of the two different test antigens and a common bound component. The common bound component may be, for example, antibodies or proteins in or from a test subject sample. Formation of the complex can allow generating a detectable signal from at least one of the two different test antigens; and permits using each of the at least two different test antigens as a cross-reactive control antigen.

In an embodiment of the present invention, the method comprises establishing or basing a quantitative threshold to determine risk of result bias based on cross-reactivity. This threshold is based on observable data generated by the in vitro formation of complexes involving target antigen and complexes involving CCAs. This threshold may vary and can be determined based on observable data generated for different test antigens and CCAs under study.

The following examples are offered by way of illustration, and not by way of limitation.

EXAMPLES

Example 1

Preparation of ZIKV-Derived Virus-Like Particles (VLPs)

In this example, VLPs of Zika virus are prepared.

Genomic RNA was extracted from 150 µl of Vero cell culture medium infected with Zika virus (ZIKV) strain MR766 using a QIAamp viral RNA kit (Qiagen, Santa Clarita, Calif.). Extracted RNA was re-suspended in 80 μl of diethyl pyrocarbonate-treated water (Sigma, St. Louis, Mo.) and used as a template in a reverse transcriptase-PCR (RT-PCR) for the amplification of ZIKV prM and E genes.

Amplification primers were designed based on the published ZIKV MR766 sequence (GenBank: LC002520.1) with a AfeII restriction enzyme site incorporated at the 5' terminus of the cDNA amplicon, and an in-frame termination codon followed by a NotI restriction site was introduced at the 3' terminus. A single cDNA fragment containing genomic nucleotides (nt) 482 to 2488 was amplified by reverse transcriptase-mediated PCR (RT-PCR) using a Titan RT-PCR Kit (Roche Molecular Biochemical, Indianapolis, Ind.). The RT-PCR product was purified using a QIAquick PCR purification kit (Qiagen), and the DNA was eluted with 50 μl of 1 mM Tris-HCl (pH 7.5). The ZIKV virus cDNA amplicon was digested with AfeII and NotI enzymes, and the resulting fragment was inserted into pcDD1 vector digested with AfeII and NotI sites of to make pcDZMR. The pcDZMR plasmid contains the cytomegalovirus early gene promoter and transcriptional control element and an engineered Japanese Encephalitis virus (JEV) signal sequence element in frame with the ZIKV prM/E sequence. The ZIKV prM/E gene sequence was verified by bi-directional sequencing.

For plasmid transformation into mammalian cells, COS-1 cells were grown to 75% confluence in 150-cm$^2$ culture flasks, trypsinized, and re-suspended in 4° C. phosphate-buffered saline (PBS) to a final density of 1-2×10$^7$cells/ml. Five hundred µl of cell suspension was then electroporated with 10 µg of plasmid DNA, using a Bio-Rad Gene Pulser II set at 250 V and 960 µF. Cells were diluted with 25 ml of fresh medium after electroporation and seeded into one 75-cm2 flask. 48 hours after transformation, the medium was removed and replaced with fresh culture medium containing 0.5 mg/ml G418 (Sigma). After 2-3 weeks of selection, G418-resistant colonies were cloned by limited dilution in G418-containing medium. Expression of ZIKV VLPs in the media culture supernatants was verified using the flavivirus E protein-specific mAb 4G2.

Example 2

Preparation of Cross-Reactive Control Antigen (CCA)

The Cross-reactive Control Antigen (CCA) is prepared using a mixture of Dengue and West Nile Virus-derived VLPs, generated as for the target antigen. The relative amount of each VLP in the mixture can be optimized by evaluating varying concentrations of Dengue and WNV VLPs independently against samples known to have anti-Zika virus IgM, anti-Dengue virus IgM, anti-WNV virus IgM, and against normal samples from uninfected subjects. Mixtures of varying ratios of WNV and Dengue VLPs are also evaluated against the samples. The ratio that yields the biggest signal spread between Dengue/WNV and Zika is chosen.

Example 3

Preparation of Normal Cell Antigen (NCA)

The Normal Cell Antigen (NCA) is prepared by collecting supernatant from the same cell line (COS-1) that is used to express the Zika VLP and Cross-reactive Control Antigen (CCA). The NCA is diluted at an appropriate concentration in the same diluents used with the Zika VLP and CCA. The NCA provides an additional internal control to aid in the proper classification of sample status.

Example 4

IGM Capture ELISA Assay

In this Example, the procedure to perform an IgM capture ELISA with test serum from a subject is described.

Positive and negative controls should be assayed in duplicate with the ZIKV Antigen (Zika Ag), Cross-reactive Control Antigen (CCA) and Normal Cell Antigen (NCA) portions of assay. Unknown serum samples to be tested can be assayed singly with the Zika Ag, CCA and NCA.

Test sera and controls are diluted to 1:100 using Sample Dilution Buffer, containing goat serum and trace non-ionic detergent in a Tris based buffer, pH 7.4.

Figure 1B:
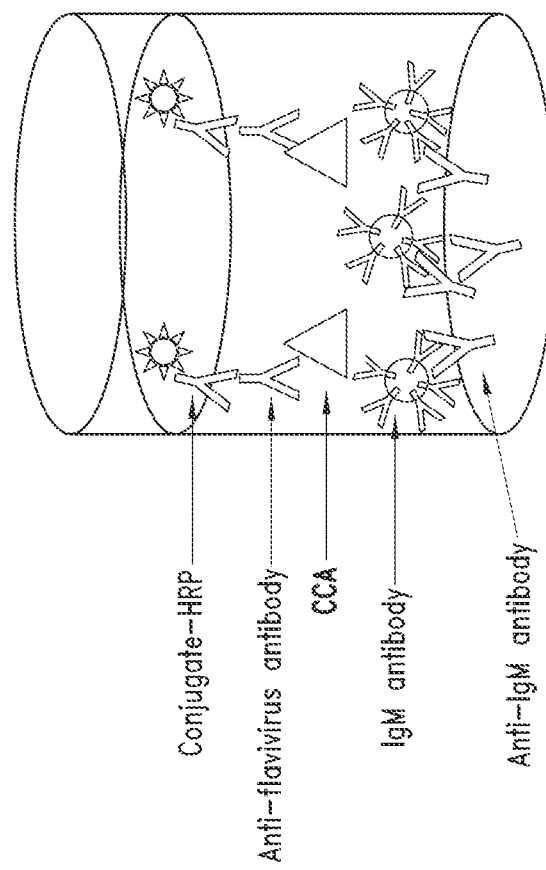
FIG. 1B depicts an ELISA-type assay wherein anti-IgM capture antibodies are immobilized in an assay well, IgM antibodies are bound by the capture antibodies forming antibody-antibody complexes, the antibody-antibody complex is cross-reactive with a CCA (e.g., DENV VLP) forming a CCA-immune complex, an anti-flavivirus antibody is bound to the CCA, and an HRP-conjugated antibody is bound to the anti-flavivirus antibody.
Figure 1C:
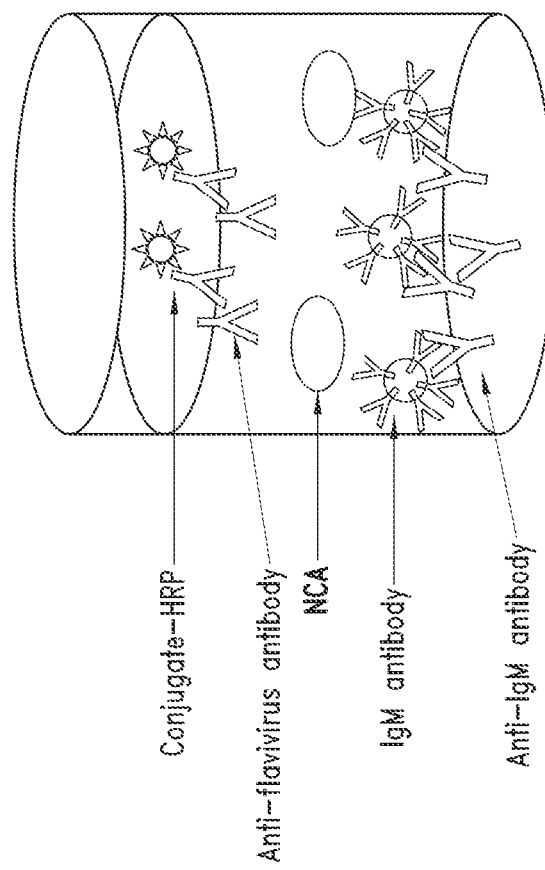
FIG. 1C depicts an ELISA-type assay wherein anti-IgM capture antibodies are immobilized in an assay well, IgM antibodies are bound by the capture antibodies forming antibody-antibody complexes, and the antibody-antibody complex is cross-reactive with a NCA forming an NCA-immune complex. The anti-flavivirus antibody does not bind the NCA, and the HRP-conjugated antibody and the anti-flavivirus antibody will be washed out of the assay well prior to detection.

Anti-IgM capture antibodies are immobilized in each assay well. See e.g., the "Anti-IgM antibody" depicted in each of FIG. 1A, FIG. 1B, and FIG. 1C. To each well is added 50 µL diluted test sera, ZIKV IgM Negative Control, and ZIKV IgM Positive Control. The top of the plate is covered, e.g., with Parafilm® to ensure even temperature distribution in all wells from bottom and sides.

The plate is incubated at 37° C. for 1 hour in a non-gas incubator. The anti-IgM capture antibodies bind IgM antibodies present in the test sera or in the controls (if present), respectively. After incubation, the plate is washed multiple (e.g., 6) times using approximately 300 µL or 1× wash buffer made of a phosphate based buffer containing 0.1° A tween-20, pH 7.4. in each wash cycle.

Per well, 50 µL of one of Zika Ag, CCA and NCA is added. See e.g., FIG. 1A (the "Zika VLP"), FIG. 1B (the "CCA"), and FIG. 1C (the "NCA"). The plate is covered and incubated at 37° C. for 1 hour in a non-gas incubator. Following incubation, the plate is washed as described above. An exemplary plate layout for a 96-well plate is depicted in FIG. 2.

A freshly prepared conjugate solution is made by diluting the appropriate volumes of 100× enzyme conjugate (i.e., a labeled antibody such as, for example, an HRP labeled anti-mouse IgG or a labeled primary antibody) into the conjugate diluent (1 part:100 parts). The enzyme conjugate comprises anti-flavivirus antibody that can bind to the Zika Ag and the CCA, but not the NCA. See e.g., FIG. 1A, FIG. 1B, and FIG. 1C. The conjugate diluent contains nonfat dry milk and trace non-ionic detergent in a tris based buffer, pH 7.4. 50 µL of conjugate solution is added to each well. The top of the plate is covered, and the plate is incubated at 37° C. for 1 hour in a non-gas incubator. Following incubation, the plate is washed (e.g., 6 times) using 1× wash buffer. Chromogenic substrate, such as horse radish peroxidase (HRP), that can bind to the Zika Ag, the CCA, and the NCA is added (75 µL/well). See e.g., the "Conjugate-HRP" in each of FIG. 1A, FIG. 1B, and FIG. 1C. The uncovered plate is incubated in the dark at room temperature (20-25° C.) for 10 minutes. After the incubation, 50 µL/well of stop solution (1N $H_2SO_4$) is added and the plate if further incubated for 1 minute. After the incubation, the RAW OD 450 nm value is determined.

Mean ZIKV IgM Negative Control values are calculated with ZIKV Antigen, CCA, and NCA. An exemplary negative control is shown in the table below along with calculation of the ZIKV IgM Negative Control values.

|  | $OD_{450}$ | | |
| --- | --- | --- | --- |
|  | Zika Ag | CCA | NCA |
| Replicate 1 | 0.108 | 0.103 | 0.095 |
| Replicate 2 | 0.092 | 0.110 | 0.089 |
| Sum | 0.200 | 0.213 | 0.184 |

Average Zika Ag = 0.200 ÷ 2 = 0.100
Average CCA = 0.213 ÷ 2 = 0.107
Average NCA = 0.184 ÷ 2 = 0.092

All values are similar indicating that there are not IgM antibodies to Zika or other flavivirus in the sample.

The average values are used to perform the following calculations:

Calculate the Zika Ag/CCA Ratio (Zika ISR)=Zika Ag÷CCA:

0.100÷0.107=0.935

Calculate the Zika Ag/NCA Ratio=Zika Ag÷NCA:

0.100÷0.092=1.087

Calculate the CCA/NCA Ratio=CCA÷NCA:

0.107÷0.092=1.163

The mean ZIKV IgM Positive Control values are calculated with ZIKV Antigen, CCA, and NCA. An exemplary positive control is shown in the table below.

|  | $OD_{450}$ | | |
| --- | --- | --- | --- |
|  | Zika Ag | CCA | NCA |
| Replicate 1 | 1.121 | 0.160 | 0.121 |
| Replicate 2 | 1.205 | 0.152 | 0.105 |
| Sum | 2.326 | 0.312 | 0.226 |
| Avg | 1.163 | 0.156 | 0.113 |

Max $OD_{450}$ = 1.163
Average Zika Ag = 2.326 ÷ 2 = 1.163
Average CCA = 0.312 ÷ 2 = 0.156
Average NCA = 0.226 ÷ 2 = 0.113

Zika ISR (Immune Status Ratio)=Zika Ag÷CCA ratio: 1.163÷0.156=7.455

MAX ISR E Max $OD_{450}$ (here the average Zika Ag)÷NCA ratio: 1.163÷0.113=10.292

The ISR for Zika is within a range indicating that there is IgM anti-Zika virus in the serum sample.

The table below shows values for positive and negative controls in typical assays. These values must be obtained in order to report results of the assay as non-fulfillment of these criteria is an indication to reagents or test procedure error requiring repetition of the assay.

| Factor (For Assay Verification) | Tolerance |
| --- | --- |
| Mean Negative Control $OD_{450}$ with Zika Antigen | <0.300 |
| Mean Positive Control $OD_{450}$ in Zika Antigen | >0.300 |
| Positive Control Zika Immune Status Ratio (ZIKA ISR) | >3.0 |
| Positive Control MAX Immune Status Ratio (MAX ISR) | >3.0 |
| Negative Control Zika Immune Status Ratio (ZIKA ISR) | <1.7 |
| Negative Control Zika Immune Status Ratio (MAX ISR) | <1.7 |

Example 5

Calculation and Interpretation of Results

This example teaches a method of calculating the relative amounts of IgM antibodies to the test agent and to the cross-reacting agent(s) and how to determine which agent the subject was infected with.

Properly interpreting specimen data includes the following steps: (1) determine the Zika ISR value for each specimen; (2) evaluate the Zika ISR value and determine the preliminary sample status as "Reactive for Zika IgM", "NCA Analysis Required" or "Re-Test". See FIG. 3, the Zika Interpretation Table. If a sample is considered "Reactive for Zika IgM", no further analysis is required; (3) determine if a sample falls in the "Re-Test" range. If the sample is considered "Re-Test", the specimen should be re-run according to the instructions for use in duplicate using Zika Ag, CCA and NCA. The Zika ISR is then re-calculated using the average values from the duplicate re-test run and interpreted according to the Zika Interpretation Table (see FIG. 3); (4) if a sample is considered "NCA Analysis Required", then calculate both the Zika Ag NCA Ratio and the CCA NCA Ratio. NCA Analysis will also be necessary for a "Re-Test" specimen whose average Zika ISR after re-testing is <1.70; and (5) evaluate results using the Zika Interpretation Table.

As indicated above, a number of relevant figures are used in the evaluation, including the following figures.

Zika Ag $OD_{450}$: This is the raw $OD_{450}$ value obtained with a specimen using the ZIKV Antigen (e.g., VLP).

CCA $OD_{450}$: This is the raw $OD_{450}$ value obtained with a specimen using the Cross-reactive Control Antigen (e.g., VLP).

NCA $OD_{450}$: This is the raw $OD_{450}$ value obtained with a specimen using the Normal Cell Antigen (NCA).

ZIKA ISR: This is the ratio of the Zika Ag $OD_{450}$ to the CCA $OD_{450}$. That is, ZIKA ISR=Zika Ag $OD_{450}$÷CCA $OD_{450}$.

ZIKA/NCA Ratio: This is the ratio of the Zika Ag $OD_{450}$ to the NCA $OD_{450}$. That is, Zika Ag OD 450÷NCA $OD_{450}$.

CCA/NCA Ratio: This is the ratio of the CCA $OD_{450}$ to the NCA $OD_{450}$. That is, CCA OD 450÷NCA $OD_{450}$.

MAX $OD_{450}$: This is the maximum raw OD450 value obtained for a given specimen from EITHER the Zika Ag $OD_{450}$ or the CCA $OD_{450}$. That is, MAX $OD_{450}$=max (Zika Ag $OD_{450}$, CCA $OD_{450}$).

MAX ISR: This is the ratio of the MAX $OD_{450}$ to the NCA $OD_{450}$. That is, MAX ISR=MAX $OD_{450}$ NCA $OD_{450}$.

First, the Zika ISR value is determined. A Table 1 setting out exemplary criteria for interpretation of the Zika ISR value is below.

| ZIKA ISR | Result | Interpretation |
| --- | --- | --- |
| ZIKA ISR ≤1.60 | Non-Reactive for Zika IgM antibodies | No detectable IgM antibody, individual does not appear to have recent infection with ZIKV. To evaluate whether there has been infection with other Flaviviruses, determine the MAX ISR value. An additional sample may be tested within 7-14 days if early infection is suspected. |
| 1.6 < ZIKA ISR < 1.8 | Re-test | Sample may be re-assayed in duplicate to confirm the final status. |
| ZIKA ISR ≥1.80 | Reactive for Zika IgM antibodies | Presence of detectable IgM antibody, possible recent infection with ZIKV.. |

If a sample falls in the "Re-test" range, this sample may be re-tested, preferably in duplicate, following the procedure disclosed herein. The average ISR value from these duplicate samples is then be interpreted as non-reactive if the ISR is <1.7 and reactive if the ISR is ≥1.7.

Overall, the following table may be used for interpretation of results.

| Scenario | Result | Interpretation |
|---|---|---|
| ZIKA ISR <1.70 AND MAX ISR <1.70 | Non-Reactive for Zika IgM antibodies | No detectable IgM antibody, individual does not appear to have recent infection with ZIKV. An additional sample may be tested within 7-14 days if early infection is suspected. |
| ZIKA ISR <1.70 AND MAX ISR ≥1.70 | Reactive for other possible flavivirus infection | Presence of detectable IgM antibody targeting a flavivirus may be present. |
| ZIKA ISR ≥1.70 | Reactive for Zika IgM antibodies | Presence of detectable IgM antibody, possible recent infection with ZIKV. |

For additional clarity, provided below are four example specimens with sample data for evaluation:

|  | Zika Ag OD450 | CCA OD450 | NCA OD450 |
|---|---|---|---|
| Sample #1 | 1.379 | 0.085 | 0.062 |
| Sample #2 | 0.120 | 0.946 | 0.049 |
| Sample #3 | 0.131 | 0.416 | 0.102 |
| Sample #4 | 0.114 | 0.099 | 0.108 |

Step 1: Determine the Specimen's Zika ISR

Zika ISR=Zika Ag OD450÷CCA OD450. The four example specimens would then have the following Zika ISR values:

|  | Zika ISR |
|---|---|
| Sample | 16.22 |
| Sample | 0.13 |
| Sample | 0.31 |
| Sample | 1.15 |

Step 2: Evaluate the Specimen's Zika ISR

We first look at ISR Analysis columns of the Zika Interpretation Table to evaluate the initial result. The four example specimens would then have the following preliminary interpretations:

|  | Preliminary Interpretation |
|---|---|
| Sample #1 | Reactive for Zika IgM |
| Sample #2 | NCA Analysis Required |
| Sample #3 | NCA Analysis Required |
| Sample #4 | NCA Analysis Required |

Step 3: Determine if a Sample Falls in the "Re-Test" Range

Reviewing the Zika Interpretation Table indicates that none of these example specimen values fall in the "re-test" range. Therefore, no duplicate testing would be required for any of these specimens.

|  | Duplicate testing required? |
|---|---|
| Sample #1 | No |
| Sample #2 | No |
| Sample #3 | No |
| Sample #4 | No |

Step 4: If the Sample is Considered "NCA Analysis Required", then Calculate Both the Zika NCA Ratio and the CCA÷NCA Ratio The four example specimens would then have the following ratios:

|  | Zika ÷ NCA Ratio | CCA ÷ NCA Ratio |
|---|---|---|
| Sample #1 | No NCA Analysis Required (Reactive for Zika IgM) | No NCA Analysis Required (Reactive for Zika IgM) |
| Sample #2 | 2.45 (0.120 ÷ 0.049) | 19.31 (0.946 ÷ 0.049) |
| Sample #3 | 1.28 (0.131 ÷ 0.102) | 4.08 (0.416 ÷ 0.102) |
| Sample #4 | 1.06 (0.114 ÷ 0.108) | 0.92 (0.099 ÷ 0.108) |

Step 5: Evaluate the Results Using the Interpretation Table

Evaluate each ratio using the Zika Interpretation Table. The four example specimens would then have the following final interpretations:

|  | Interpretation |
|---|---|
| Sample #1 | Presumptive Zika Positive |
| Sample #2 | Possible Zika Positive |
| Sample #3 | Presumptive Other flavivirus Positive |
| Sample #4 | Negative |

Example 6

IGM Capture ELISA Assay Results on Clinical Samples

Clinical Specificity and Cross-Reactivity: The ZIKV IgM ELISA kit as described herein was tested against 217 samples, including 89 normal human serum, 89 specimens that were infected with other, non-flavivirus diseases and 32 flavivirus IgM positive specimens. An additional 7 yellow fever vaccine recipients were included for this study. Of the 89 normal human samples (negative), none were reactive for Zika or cross-reactive antigens. Additionally, none of the "other disease" (non-Flavivirus) specimens was reactive in the ELISA kit. Of the 32 IgM flavivirus specimens (non-Zika), 31 were correctly categorized as "Other flavivirus possible . . . ". None of the 32 IgM flavivirus specimens was considered Zika Reactive in the ELISA kit. One of the flavivirus specimens tested as "Non-Reactive" in the ZIKV Detect IgM ELISA kit. Of the 7 yellow fever vaccine recipients, 2 were classified as "Other flavivirus possible . . . ".

The negative percent agreements for each category of specimen are shown below. The positive percent agreement for correctly classifying IgM positive flavivirus specimens as "Other flavivirus possible . . . " is also indicated below. This is separate from the positive percent agreement that is established for Zika IgM positive specimens (considered "Zika Reactive").

The potential cross-reactivity with other diseases was evaluated by testing specimens from patients with confirmed IgM antibodies to other microorganisms which could potentially cause false positive results. This list is composed of organisms whose infection produces symptoms similar to those observed at the onset of Zika virus infection and also viral strains which have a significant likelihood to result in cross-reactivity due to genetic similarity with Zika virus. Also included were organisms/strains which are likely to be observed in the currently affected and endemic areas (i.e., Brazil and South America) since these organisms/strains will be an important part of the differential diagnosis of Zika virus infection.

|  | Sample Status | | | | |
| --- | --- | --- | --- | --- | --- |
|  | Negative (normal) | Other Disease (non-Flavivirus) | Flavivirus (non-Zika) | Yellow Fever Vaccine Recipients | Total |
| Non-Reactive | 89 | 89 | 1 | 5 | 184 |
| Other Flavivirus | 0 | 0 | 31 | 2 | 33 |
| Zika Reactive | 0 | 0 | 0 | 0 | 0 |
| Total | 89 | 89 | 32 | 7 | 217 |
| Negative Percent Agreement (normal): | 100% (89/89, 95.9%-100%) | | | | |
| Negative Percent Agreement (Other Disease): | 100% (89/89, 95.9%-100%) | | | | |
| Negative Percent Agreement (for Flavivirus, non-Zika)*: | 100% (32/32, 89.3%-100%) | | | | |
| Negative Percent Agreement for Yellow Fever Vaccine Recipients (considered "Zika Non-Reactive"):** | 100% (7/7, 64.6%-100%) | | | | |
| Total Negative Percent Agreement: | 100% (217/217, 98.3%-100%) | | | | |
| Positive Percent Agreement (for Flavivirus, non-Zika)†: | 96.9% (31/32, 84.3%-99.4%) | | | | |

*These flavivirus positive specimens screened as non-reactive for Zika.
**Note: while none of the YFV recipients were considered Zika Reactive, 2 of the 7 were considered "Other Possible Flavivirus . . . "
†These flavivirus positive specimens screened as "Other Possible Flavivirus . . . "

Thirteen archived Zika IgM confirmed samples (confirmed via CDC MAC ELISA and/or PCR) were tested using IgM Capture ELISA as described herein. All 13 samples were reactive for Zika virus. This estimates a Positive Percent Agreement of 100% (13/13, 77.2%-100%) for these samples. [All confidence intervals presented are 95% confidence intervals using the Wilson Score method.]

In a field study in Puerto Rico 44 samples representing a mixture of normal, confirmed Zika IgM positive and confirmed Dengue IgM positive specimens (PCR positive for Dengue) were tested. Additionally, paired serum samples collected from 21 individuals (42 total samples), collected during acute and convalescent time points, were tested. All acute samples were confirmed Zika positive by PCR at CDC. The mean number of days post onset of symptoms was ~2.2 days (range 1-5 days). The mean number of days post onset of symptoms for the convalescent sample was ~15.9 days (range 6-80 days). The IgM Capture ELISA detected all 21 individuals at the convalescent time point. Additionally, three individuals were considered reactive with the IgM Capture ELISA at the acute phase (days 1, 4 and five post onset of symptoms). None of the samples had values warranting a re-test.

The above data are combined into the table below. The Final Interpretation is determined by the following method: if a sample is PCR positive (for Zika or Dengue), then this is considered final. Otherwise, the CDC Zika MAC-ELISA result is subsequently considered as the final diagnosis for these analysis purposes.

|  | Disease/ Infectious agent Positive Sera | # of samples | # Zika Reactive | # Other Flavivirus Possible | # Non-Reactive | % False "Zika Reactive" | % False "Other Flavivirus Possible" |
| --- | --- | --- | --- | --- | --- | --- | --- |
| Other disease present (IgM Positive) | Anti-Chikungunya virus | 8 | 0 | 0 | 8 | 0% | 0% |
|  | Anti-Cytomegalovirus (CMV) | 10 | 0 | 0 | 10 | 0% | 0% |
|  | Anti-Epstein Barr Virus (EBV) -CA | 15 | 0 | 0 | 15 | 0% | 0% |
|  | Anti-Parvovirus B19 | 5 | 0 | 0 | 5 | 0% | 0% |
|  | Anti-Varicella zoster virus | 10 | 0 | 0 | 10 | 0% | 0% |
|  | Anti-nuclear Antibodies (ANA) | 10 | 0 | 0 | 10 | 0% | 0% |
|  | Rheumatoid Factor | 11 | 0 | 0 | 11 | 0% | 0% |
|  | HAMA (human anti-mouse antibody) | 3 | 0 | 0 | 3 | 0% | 0% |
|  | Anti-Malaria/anti-plasmodium falciparum | 7 | 0 | 0 | 7 | 0% | 0% |
|  | Anti-Hepatitis (C) virus | 10 | 0 | 0 | 10 | 0% | 0% |
| Flavivirus Specimens (non-Zika, IgM Positive) | Anti-Dengue virus | 14 | 0 | 14 | 0 | 0% | 0% |
|  | Anti-West Nile Virus | 13 | 0 | 13 | 0 | 0% | 0% |
|  | Anti-Japanese Encephalitis | 1 | 0 | 1 | 0 | 0% | 0% |
|  | Anti-Saint Louis encephalitis (SLE) | 4 | 0 | 3 | 1 | 0% | 0% |
| Immunization to Flavivirus | Yellow fever virus post-immunization | 7 | 0 | 2 | 5 | 0% | N/A* |

*Individuals immunized against a flavivirus may be considered false negative or false positive with a reaction that classifies the specimen as "other flavivirus possible . . ."

|  |  | Final Interpretation | | | | |
| --- | --- | --- | --- | --- | --- | --- |
|  |  | Positive | Equivocal | Negative | Dengue | Total |
| IgM Capture ELISA | Reactive | 38 | 2 | 0 | 0 | 40 |
|  | Other Flavivirus | 1[a] | 0 | 3[b] | 9[c] | 13 |
|  | Non-Reactive | 0 | 0 | 12 | 0 | 12 |
|  | Total: | 39 | 2 | 15 | 9 | 65 |

[a]This sample was also positive for Dengue IgM antibodies, and cross-reactivity should be considered. This was classified as Zika positive based solely on the CDC MAC-ELISA results.
[b]All 3 "Other Flavivirus" reactions were Positive for Dengue IgM antibodies with an IgM Capture ELISA to detect anti-Dengue virus IgM antibodies.
[c]These 9 specimens were confirmed Dengue positive by PCR and classified as such.

Combining all data (from 13 confirmed Zika specimens) (n=13) and the specificity and cross-reactivity data (n=217) with the testing at Puerto Rico (n=65), the following overall performance characteristics for 295 total samples by IgM Capture ELISA are summarized in the table below.

|  | Sample Status | | | | | | |
| --- | --- | --- | --- | --- | --- | --- | --- |
| InBios ZIKV Detect ™ IgM ELISA | Zika Positive | Equivocal | Other Disease (non-Flavivirus) | Flavivirus (non-Zika) | Yellow Fever Vaccine Recipients | Negative (normal) | Total |
| Zika Reactive | 51 | 2 | 0 | 0 | 0 | 0 | 53 |
| Other Flavivirus | 1[a] | 0 | 0 | 40 | 2 | 3[b] | 46 |
| Non-Reactive | 0 | 0 | 89 | 1 | 5 | 101 | 196 |
| Total | 52 | 2 | 89 | 41 | 7 | 104 | 295 |

[a]This sample was also positive for Dengue IgM antibodies and cross-reactivity should be considered. This was classified as Zika positive based solely on the CDC MAC-ELISA results
[b]All 3 of these "Other Flavivirus Possible" reactions were Positive for Dengue IgM antibodies with the DENV Detect IgM Capture ELISA.

| | |
| --- | --- |
| Positive Percent Agreement (for presumptive Zika Positive): | 98.1% (51/52, 89.9%-99.7%)[a] |
| Positive Percent Agreement (for Flavivirus, non-Zika)[b]: | 97.6% (40/41, 87.4%-99.6%) |
| Negative Percent Agreement (normal): | 97.1% (101/104, 91.9%-99.0%)[c] |
| Negative Percent Agreement (Other Disease): | 100% (89/89, 95.9%-100%) |
| Negative Percent Agreement (for Flavivirus, non-Zika)[d]: | 100% (41/41, 91.4%-100%) |
| Negative Percent Agreement (for Yellow Fever Vaccine Recipients, considered "Zika Non-Reactive")[e]: | 100% (7/7, 64.6%-100%) |
| Total Negative Percent Agreement: | 98.8% (238/241, 96.4%-99.6%) |

[a]The one specimen missed here tested as "Other Flavivirus Possible" and was also positive for Dengue IgM antibodies.
[b]These flavivirus positive specimens screened as "Other Flavivirus Possible . . . "
[c]All 3 of these false positive specimens were classified as "Other Flavivirus Possible" and were Positive for Dengue IgM antibodies with the DENV Detect IgM Capture ELISA.
[d]These are the flavivirus positive specimens that screened as non-reactive for Zika.
eNote: while none of the YFV recipients were considered Zika Reactive, 2 of the 7 were considered "Other Flavivirus Possible . . . "

Interference testing: Potentially interfering substances commonly occurring in serum were evaluated with the IgM Capture ELISA. Interfering substances included bilirubin (0.2 mg/mL), hemoglobin (160 mg/mL), albumin (150 mg/mL) and cholesterol (5 mg/mL). These interfering substances were spiked into low reactive (n=3) and normal human serum samples (n=3) to evaluate their impact on assay performance. None of the interfering substances caused a statistically significant change in the ISR value for either the low reactive samples or normal human serum samples evaluated and did not alter the interpretation results.

Additionally, 3 human anti-mouse antibody (HAMA) serum samples and 3 rheumatoid factor (RF) positive serum samples were acquired from commercial vendors. Each HAMA and RF sample was mixed with a Zika low reactive specimen (ISR ~2.5) in the kit sample dilution buffer (equivalent to a 1:1 dilution of the Zika sample:Interfering sample) and the assay was performed as described herein. Of the 3 HAMA samples, none altered the reactivity of the low positive. Of the 3 RF samples, 2 out of the 3 (66.6%) diminished the ISR value substantially enough to alter the sample from a "Reactive" status to a "Non-Reactive" status.

| Interfering Substance | Concentration Tested | Effect on Low Reactive Specimens | Effect on Negative Specimens |
| --- | --- | --- | --- |
| Bilirubin | 0.2 mg/mL | None observed (0/3) | None observed (0/3) |
| Hemoglobin | 160 mg/mL | None observed (0/3) | None observed (0/3) |
| Albumin | 150 mg/mL | None observed (0/3) | None observed (0/3) |
| Cholesterol | 5 mg/mL | None observed (0/3) | None observed (0/3) |
| HAMA | Varies | None observed (0/3) | None observed (see cross-reactivity table) |
| RF | Varies | Lowered reactivity (2/3) | None observed (see cross-reactivity table) |

Example 7

The IgM ELISA as described herein was tested with serum samples known to be positive for ZIKV, DENV, WNV, or CHIKV.

The ZIKV positive serum samples were obtained from CDC panels that were confirmed by CDC MAC ELISA and PRNT. The WNV positive serum samples were sourced from a reference lab in South Dakota during a WNV outbreak. The DENV positive serum samples were sourced from a reference lab in Utah with confirmed Dengue infections. The CHIKV positive serum samples were sourced from a commercial vendor. 96-well ELISA plates were sourced from InBios International Inc. (Part #500613) and came pre-coated with anti-Human IgM antibody.

Serum specimens were diluted into a sample dilution buffer (InBios International Part #500241D) at a 1:100 dilution and added to the appropriate wells (50 µL per well). Each plate was covered and incubated at 37° C. for 1 hour.

After incubation, plates were washed 6 times with an automated ELISA plate washer (BioTek ELX405) using a phosphate buffered saline (PBS) buffer containing 0.05% tween-20.

Antigens (50 µL per well) were then directly added to the appropriate wells such that each serum specimen is incubated with ZIKV antigen (Zika VLP), DENV antigen (Dengue VLP), WNV antigen (WN VLP), CHIKV antigen (Chik VLP), CCA and NCA. The ELISA plates were covered and incubated at 37° C. for 1 hour.

After incubation, the ELISA plates were washed 6 times using an automated automated ELISA plate washer (BioTek ELX405) using a phosphate buffered saline (PBS) buffer containing 0.05% tween-20.

A cocktail of pan-flavivirus monoclonal antibodies (targeting flavivirus envelope protein) and a CHIKV antibody (targeting the Chikungunya envelope protein) were added to all of the wells. The ELISA plates were covered and incubated at 37° C. for 30 minutes.

After incubation, the ELISA plates were washed 6 times using an automated ELISA plate washer (BioTek ELX405) using a phosphate buffered saline (PBS) buffer containing 0.05% tween-20.

A conjugate solution (anti-mouse IgG-HRP) was then added to each well (50 µL per well). The ELISA plates were covered and incubated at 37° C. for 30 minutes.

After incubation, the ELISA plates were washed 6 times using an automated ELISA plate washer (BioTek ELX405) using a phosphate buffered saline (PBS) buffer containing 0.05% tween-20.

After washing, a TMB substrate was added to each well (75 µL per well) causing a color change proportional to the amount of HRP (horse-radish peroxidase) present in each complex.

The reaction was stopped with the addition of 50 µL of 1N $H_2SO_4$ and the raw optical density (OD) was measured at 450 nm using an ELISA plate reader.
Analysis:

The initial analysis was performed using the Zika antigen, the CCA antigen and NCA control. The CCA was comprised of a combination of Dengue antigen and West Nile antigen. An algorithm that aptly applies for discriminating between Zika, other Flaviviruses and Negative specimens can be demonstrated as such:

(1) If the raw Zika $OD_{450}$ is ≥3.0×the Negative Control $OD_{450}$ AND the Zika ISR≥1.70, then the specimen is considered Presumptive Zika Positive (2) OTHERWISE, if the CCA/NCA ratio ≥3.0, then the specimen is considered Presumptive Other Flavivirus Positive (3) OTHERWISE, the sample is considered Negative Example raw data for a panel of Zika, West Nile, Dengue, Chikungunya and normal serum samples are shown in FIG. 4A, FIG. 4B, and FIG. 5B. The assay was performed simultaneously with all of the specimens using the same buffers for all steps except for the target antigen. An example analysis using the algorithm described above is shown using data from the Zika antigen, CCA and NCA. This analysis accurately categorizes the Zika positive, Other Flavivirus and Negative serum specimens. As demonstrated in FIG. 5A, FIG. 5B, FIG. 5C, FIG. 5D, and FIG. 5E, similar analyses can be readily performed using the Dengue, West Nile and Chikungunya antigens to properly categorize these while using an appropriate CCA.

From the foregoing it will be appreciated that, although specific embodiments have been described herein for purposes of illustration, various modifications may be made without deviating from the spirit and scope of the invention. Accordingly, the invention is not limited except as by the appended claims.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

The invention claimed is:

1. A diagnostic assay comprising a common bound component, a common test antigen conjugate, and two or more different test antigens, wherein:
   i. each test antigen binds to each of the common bound component and the common test antigen conjugate;
   ii. each of the different test antigens indicates the presence or absence of a particular bound component;
   iii. the different test antigens are derived from different species within a shared viral genus, wherein the shared viral genus is selected from the flavivirus genus and the alphavirus genus;
   iv. at least one of the different test antigens is a cross-reactive control antigen; and
   v. the ratio of binding of each of the different test antigens to the common bound component indicates the likelihood of cross-reactivity error.

2. The diagnostic assay of claim 1, wherein the different test antigens are derived from two or more viruses selected from Zika virus, dengue virus, and West Nile virus, or derivations thereof.

3. The diagnostic assay of claim 1, wherein the different test antigens are derived from two of more viruses selected from Chikungunya virus, Ross River virus, Semliki Forest virus, Venezuelan equine encephalitis virus, Eastern equine encephalitis virus, and Western equine encephalitis virus, or derivations thereof.

4. The diagnostic assay of claim 1, wherein each of the different test antigens is a cross-reactive control.

5. The diagnostic assay of claim 1, wherein the different test antigens are analyzed substantially simultaneously.

6. The diagnostic assay of claim 1, wherein at least one different test antigen is a virus-like particle.

7. The diagnostic assay of claim 1, wherein the common test antigen conjugate also provides a detectable signal.

8. The diagnostic assay of claim 7, wherein a material used for the detectable signal is the same for the different test antigens.

9. The diagnostic assay of claim 7, wherein the presence or absence of each different test antigen is indicated by relative signal strength.

10. The diagnostic assay of claim 1, wherein the particular bound component is an antibody.

11. The diagnostic assay of claim 1, wherein the particular bound component is derived from a test subject sample.

12. A kit comprising the diagnostic assay of claim 1.

13. A method for distinguishing between related infective agents in vitro, comprising: generating a detectable signal from at least one of at least two different test antigens; and using each of the at least two different test antigens as a cross-reactive control antigen; wherein
  i. each test antigen binds to each of a common bound component and a common test antigen conjugate;
  ii. each of the different test antigens indicates the presence or absence of a particular bound component; and
  iii. the different test antigens are derived from different species within a shared viral genus, wherein the shared viral genus is selected from the flavivirus genus and the alphavirus genus.

14. The method of claim 13, further comprising: establishing a threshold based on detectable signal strength; and distinguishing between the related infective agents based on relative signal strength.

15. The method of claim 13, further comprising including a test antigen to an unrelated infective agent, wherein the unrelated infective agent produces similar symptoms in a test subject or is an infective agent to which the test subject may have been exposed.

16. The method of claim 13, wherein the related infective agents are selected from the Zika virus, dengue virus, and West Nile virus, or derivations thereof.

17. The method of claim 13, wherein the related infective agents are selected from the Chikungunya virus, Ross River virus, Semliki Forest virus, Venezuelan equine encephalitis virus, Eastern equine encephalitis virus, and Western equine encephalitis virus, or derivations thereof.

18. The method of claim 15, wherein the unrelated infective agent is chikungunya.

19. The diagnostic assay of claim 1, wherein the common bound component comprises IgM antibodies.

20. The diagnostic assay of claim 1, wherein the particular bound component is an IgM antibody that binds at least one test antigen.

21. The kit of claim 12, wherein the kit comprises anti-IgM antibodies, normal cell antigen, a negative control sample, a positive control sample, a detecting agent and buffers, and wherein the anti-IgM agent, and buffers for use with each of the different test antigens are the same.

\* \* \* \* \*